US008257712B2

(12) United States Patent
Morrison et al.

(10) Patent No.: US 8,257,712 B2
(45) Date of Patent: Sep. 4, 2012

(54) VIRUS-EXPRESSING HOST COSTIMULATION MOLECULES

(75) Inventors: Lynda A. Morrison, Webster Groves, MO (US); Lydia G. Thebeau, Eureka, MO (US); Jane E. Schrimpf, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 38 days.

(21) Appl. No.: 12/497,597

(22) Filed: Jul. 3, 2009

(65) Prior Publication Data
US 2010/0098726 A1 Apr. 22, 2010

Related U.S. Application Data

(60) Provisional application No. 61/078,196, filed on Jul. 3, 2008.

(51) Int. Cl.
*A61K 39/245* (2006.01)
(52) U.S. Cl. .................................. 424/199.1; 424/231.1
(58) Field of Classification Search ........................ None
See application file for complete search history.

(56) References Cited

U.S. PATENT DOCUMENTS

| | | | |
|---|---|---|---|
| 4,818,678 A | | 4/1989 | Oldstone et al. |
| 5,738,852 A | * | 4/1998 | Robinson et al. ........... 424/199.1 |
| 6,051,428 A | * | 4/2000 | Fong et al. ..................... 435/456 |
| 7,064,111 B1 | * | 6/2006 | Todo et al. ................... 514/44 R |
| 7,223,411 B1 | | 5/2007 | Knipe et al. |
| 2002/0147167 A1 | * | 10/2002 | Armstrong et al. ............. 514/44 |
| 2003/0021770 A1 | | 1/2003 | Schlom et al. |

FOREIGN PATENT DOCUMENTS
WO        WO 9714808        *    4/1997

OTHER PUBLICATIONS

Freund et al (International Journal of Cancer 85:508-517, 2000).*
Thebeau et al (Journal of Virology 81:12200-12209, 2007).*
Fukuhara et al (Cancer Resarch 65:10663-10668, 2005).*
Ino et al (Clinical Cancer Research 12:643-652, 2006).*
Nam et al (Acta virologica 51:125-130, 2007).*
Nunez et al (Immunologic Research 30:105-124, 2004).*
Breakefield et al (Stem Cell Biology and Gene Therapy, 1998).*
Product List. "Costimulatory Molecule & Costimulation" <<http://www.sinobiological.com/Costimulation-Costimulatory-Molecule-a-704.html>> Downloaded from the internet Jun. 24, 2011.*
Product list. "Co-stimulatory Molecules—R&D Systems" <<http://www.rndsystems.com/molecule_group.aspx?g=685&r=1>> Downloaded from the internet Jun. 24, 2011.*
Subudhi et al (Journal of Molecular Medicine 83:193-202, 2005).*
Croft (Cytokine and Growth Factor Reviews 14:265-273, 2003).*
Keadle et al (Journal of Virology 3615-3625, 2002).*
Watts et al (Canadian Journal of Infectious diseases 14:221-229, 2003).*

Ashley, R, A. Wald, and L. Corey. Cervical antibodies in patients with oral herpes simplex virus type 1(HSV-1) infection: local anamnestic responses after genital HSV-2 infection. Journal of Virology. 1994. vol. 68, No. 8: pp. 5284-5286, by American Society for Microbiology.
Ashley, R. L., L. Corey, J. Dalessio, P. Wilson, M. Remington, G. Barnum, and P. Trethewey. Protein-specific cervical antibody responses to primary genital herpes simplex virus type 2 infections. The Journal of Infectious Diseases. 1994. vol. 170: pp. 20-26, by The University of Chicago.
Babu, J. S., J. Thomas, S. Kanangat, L. A. Morrison, D. M. Knipe, and B. T. Rouse. Viral replication is required for induction of ocular immunopathology by herpes simplex virus. Journal of Virology. 1996. vol. 70, No. 1: pp. 101-107, by American Society for Microbiology.
Barcy, S., and L. Corey. Herpes simplex inhibits the capacity of lymphoblastoid B cell lines to stimulate CD4+ T cells. The Journal of Immunology. 2001. vol. 166: pp. 6242-6249, by The American Association of Immunologists, Inc.
Bertram, E. M., W. Dawicki, and T. H. Watts. Role of T cell costimulation in anti-viral immunity. Seminars in Immunology. 2004. vol. 16: pp. 185-196, by Elsevier Ltd.
Bluestone, J. A. New perspectives of CD28-B7-mediated T cell costimulation. Immunity. 1995. vol. 2: pp. 555-559, by Cell Press.
Bonneau, H. H. and S. R Jennings. Modulation of acute and latent herpes simplex virus infection in C57BL/6 mice by adoptive transfer of immune lymphocytes with cytolytic activity. Journal of Virology. 1989. vol. 63, No. 3: pp. 1480-1484, by American Society for Microbiology.
Borriello, F., M. P. Sethna, S. D. Boyd, A. N. Schweitzer, E. A. Tivol, D. Jacoby, T. B. Strom, E. M. Simpson, G. J. Freeman, and A. H. Sharpe. B7-1 and B7-2 have overlapping, critical roles in immunoglobulin class switching and germinal center formation. Immunity. 1997. vol. 6: pp. 303-313, by Cell Press.
Bosnjak, L., M. Miranda-Saksena, D. M. Koelle, R. A. Boadel, and C. A. Jones. Herpes simplex virus infection of human dendritic cells induces apoptosis and allows cross-presentation via uninfected dendritic cells. The Journal of Immunology. 2005. vol. 174: pp. 2220-2227, by The American Association of Immunologists, Inc.
Brehm, M. A., R H, Bonneau, D. M. Knipe, and S. S. Tevethia. Immunization with a replication-deficient mutant of herpes simplex virus type 1 (HSV-1) induces a CD8 (+) cytotoxic T-lymphocyte response and confers a level of protection comparable to that of wild-type HSV-1. Journal of Virology. 1997. vol. 71, No. 5: pp. 3534-3544, by American Society for Microbiology.

(Continued)

*Primary Examiner* — Mary E Mosher
(74) *Attorney, Agent, or Firm* — Mark E. Stallion, Esq.; Husch Blackwell LLP

(57) ABSTRACT

An antiviral vaccine that encodes costimulation molecules for increasing immune response to the particular virus at issue is provided herein. In an illustrative embodiment, in mice lacking both B7-1 and B7-2 (B7KO), the increased severity of HSV infection has confirmed the importance of these molecules in generation of HSV-specific immunity. To test the concept that B7-1 or B7-2 expression by replication-defective HSV could augment its immunogenicity and protective capacity, the present inventors constructed replication-defective HSV-2 encoding B7-1 or B7-2. Both viruses partially reconstituted immune responses to HSV compared with replication-defective virus alone when used to immunize B7KO mice, indicating that the increased responsiveness to virus could be attributed to virus-encoded B7 molecules.

10 Claims, 12 Drawing Sheets

OTHER PUBLICATIONS

Figure 1B:
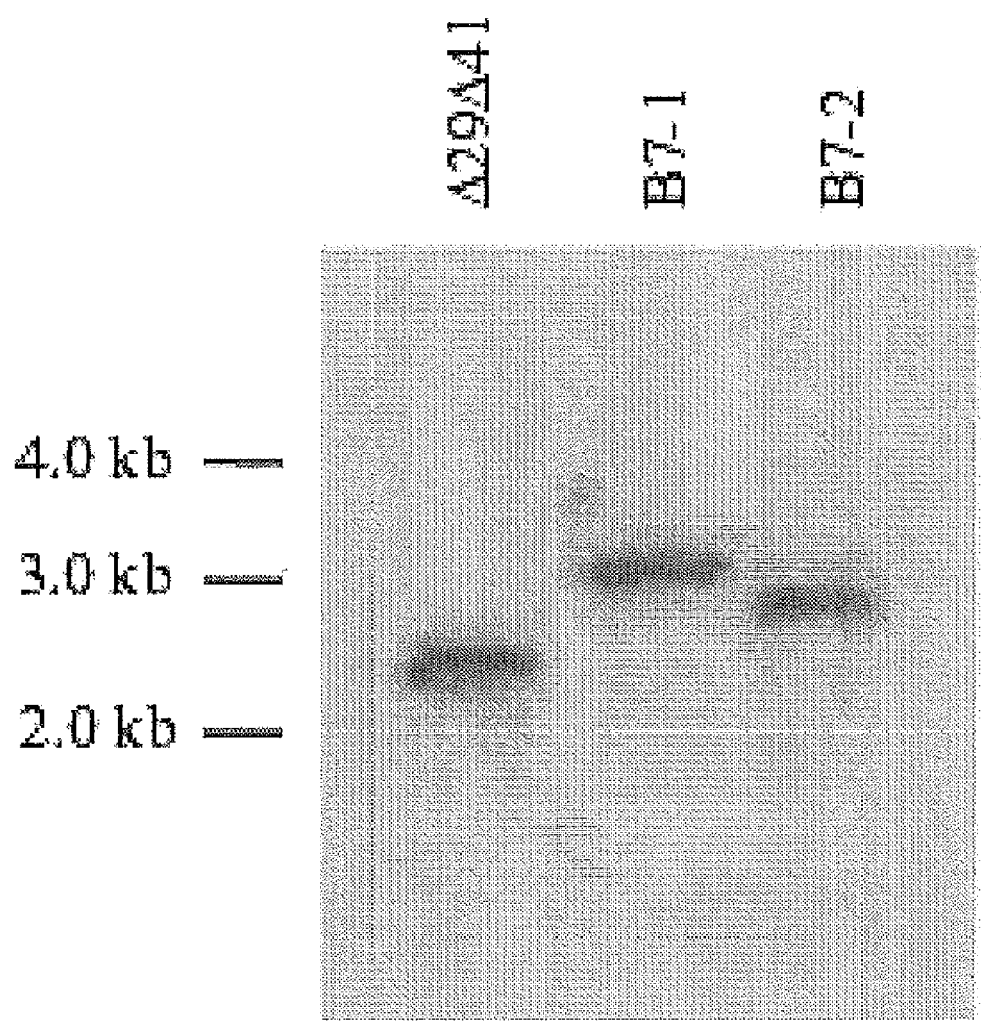

Brown, J. A., R. G. Titus, N. Nabavi, and L. H. Glimcher. Blockade of CD86 ameliorates Leishmania major infection by down-regulating the Th2 response. The Journal of Infectious Diseases. 1996. vol. 174: pp. 1303-1308 by The University of Chicago.

Brubaker, J. O., C. M. Thompson, L. A. Morrison, D. M. Knipe, G. R. Siber, and R. W. Finberg. Induction of Th1-associated immune responses to beta-galactosidase expressed by a replication-defective mutant of herpes simplex virus 1, The Journal of Immunology. 1996. vol. 157: pp. 1598-1604, by The American Association of Immunologists, Inc.

Burke, R L. Contemporary approaches to vaccination against herpes simplex virus. Current Topics in Microbiology and Immunology. 1992. vol. 179 pp. 137-158, by Springer-Verlag Berlin-Heidelberg.

Chaudhry, A., S. R. Das, A. Hussain, S. Mayor, A. George, V. Bal, S. Jameel, and S. Rath. The Nef protein of HIV-1 induces loss of cell surface costimulatory molecules CD80 and CD86 in APCs. The Journal of Immunology. 1996. vol. 175: pp. 4566-4574, by The American Association of Immunologists, Inc.

Coligan, J. E., A. M. Kruisbeek, D. H. Margulies, E. M. Shevach, and W. Strober. Measurements of Human and Murine interleukin 2 and Interleukin 4 in Current Protocols in Immunology. 1994. Published by John Wiley & Sons, Inc. vol. 1: pp. 6.3.1-6.3.13.

Coscoy, L., and D. Ganem. A viral protein that selectively downregulates ICAM-1 and B7-2 and modulates T cell costimulation. The Journal of Clinical Investigation. 2001. vol. 107, No. 12: pp. 1599-1606.

Coutelier, J. P., J. T. van der Logt, F. W. Heessen, A. Vink, and J. van Snick. Virally induced modulation of murine IgG antibody subclasses, The Journal of Experimental Medicine. 1988. vol. 168: pp. 2373-2378.

Cremer, K. J., M. Mackett, C. Wohlenberg, A. L. Notkins, and B. Moss. Vaccinia virus recombinant expressing herpes simplex virus type 1 glycoprotein D prevents latent herpes in mice. Science. 1985. vol. 228: pp. 737-739.

Da Costa, X. J., N. Bourne, L. R. Stanberry, and D. M. Knipe. Construction and characterization of a replication-defective HSV-2. Virology. 1997. vol. 232: pp. 1-12, by Academic Press.

Davar, G., M. F. Kramer, D. Garber, A. L. Roca, J. K. Andersen, W. Bebrin, D. M. Coen, M. Kosz-Vnenchak, D. M. Knipe, X. O. Breakefield, and O. Isacson. Comparative efficacy of expression of genes delivered to mouse sensory neurons with herpes virus vectors, The Journal of Comparative Neurology. 1994. vol. 339: pp. 3-11, by Wiley-Liss, Inc.

Ding, L., P. S. Linsley, L. Y. Huang, R. N. Germain, and E. M. Shevach. IL-10 inhibits macrophage costimulatory activity by selectively inhibiting the up-regulation of B7 expression. The Journal of Immunology. 1993. vol. 151, No. 3: pp. 1224-1234, by The American Association of Immunologists.

Drew, M D., A. Estrada-Correa, B. J. Underdown, and M. R McDermott. Vaccination by cholera toxin conjugated to a herpes simplex virus type 2 glycoprotein D peptide. Journal of General Virology. 1992. vol. 73: pp. 2357-2366.

Edelmann, K. H., and C. B. Wilson. Role of CD28/CD80-86 and CD40/CD154 costimulatory interactions in host defense to primary herpes simplex virus infection. Journal of Virology. 2001. vol. 75, No. 2: pp. 612-621 by American Society for Microbiology.

Elloso, M. M., and P. Scott. Expression and contribution of B7-1 (CD80) and B7-2 (CD86) in the early immune response to Leishmania major infection. The Journal of Immunology. 1999. vol. 162: pp. 6708-6715, by The American Association of Immunologists.

Farrell, H. E., C. S. McLean, C. Harley, S. Efstathiou, S. Inglis, and A. C. McLean. Vaccine potential of a herpes simplex virus type 1 mutant with an essential glycoprotein deleted. Journal of Virology. 1994. vol. 68, No. 2: pp. 927-932, by American Society for Microbiology.

Flo, J., S. Tisminetzky, and F. Baralle. Modulation of the immune response to DNA vaccine by co-delivery of costimulatory molecules. Immunology. 2000. vol. 100: pp. 259-267, by Blackwell Science Ltd.

Freeman, G. J., F. Bordello, R. J. Hodes, H. Reiser, J, G. Gribben, J. W. Ng, J. Kim, J. M. Goldberg, K. Hathcock, and G. Laszlo. Murine B7-2, an alternative CTLA4 counter-receptor that costimulates T cell proliferation and interleukin 2 production. The Journal of Experimental Medicine. 1993. vol. 178: pp. 2185-2192.

Freeman, G. J., J. G. Gribben, V. A. Boussiotis, J. W. Ng, V. A. Restivo, Jr., L. A. Lombard, G. S. Gray, and L. M. Nadler. Cloning of B7-2: a CTLA-4 counter-receptor that costimulates human T cell proliferation. Science. 1993. vol. 262: pp. 909-911.

Freeman, G. J., S. G. Gray, C. D. Gimmi, D. B. Lombard, L. Zhou, M. White, J. D. Fingeroth, J. G. Gribben, and L. M. Nadler. Structure, expression, and T cell costimulatory activity of the murine homologue of the human B lymphocyte activation antigen B7. The Journal of Experimental Medicine. 1991. vol. 174: pp. 625-631, by The Rockefeller University Press.

Freeman, G. J., V. A. Boussiotis, A. Anumanthan, G. M. Bernstein, X. Y. Ke, P. D. Rennert, G. S. Gray, J. G. Gribben, and L. M. Nadler. B7-1 and B7-2 do not deliver identical costimulatory signals, since B7-2 but not B7-1 preferentially costimulates the initial production of IL-4. Immunity. 1995. vol. 2: pp. 523-532, by Cell Press.

Gajewski, T. F., Y. Meng, and H. Harlin. Immune suppression in the tumor microenvironment. Journal of Immunotherapy. 2006. vol. 29, No. 3: pp. 233-240, by Lippincott Williams & Wilkins.

Gallichan, W. S. and K. L. Rosenthal. Specific secretory immune responses in the female genital tract following intranasal immunization with a recombinant adenovirus expressing glycoprotein B of herpes simplex virus. Vaccine. 1995. vol. 13, No. 16: pp. 1589-1595, by Elsevier Science Ltd, Great Britain.

Gallichan, W. S. and K. L. Rosenthal. Effects of the estrous cycle on local humoral immune responses and protection of intranasally immunized female mice agains herpes simplex virus type 2 infection in the genital tract. Virology. 1996. vol. 224: pp. 487-497, by Academic Press, Inc.

Gallichan, W. S. and K. L. Rosenthal. Long-lived cytotoxic T lymphocyte memory in mucosal tissues after mucosal but not systemic immunization. The Journal of Experimental Medicine. 1996. vol. 184: p. 1879-1890 by The Rockerfeller University Press.

Gao, M. and D. M. Knipe. Genetic evidence for multiple nuclear functions of the herpes simplex virus ICP8 DNA-binding protein. Journal of Virology, 1989. vol. 63, No. 12: p. 5258-5267, by American Society for Microbiology.

Gause, W. C., M. J. Halvorson, P. Lu, R Greenwald, P. Linsley, J. F. Urban, and F. D. Finkelman. The function of costimulatory molecules and the development of 1L-4-producing T cells. Immunology Today. 1997. vol. 18, No. 3: pp. 115-120, by Elsevier Science Ltd.

Goldman, Bruce, DeFrancesco, Laura. The cancer vaccine roller coaster. Nature Biotechnology. 2009. vol. 27, No. 2: pp. 129-139, by Nature America, Inc.

Grewal, L S., H. G. Foellmer, K. D. Grewal, J. Xu, F. Hardardottir, J. L. Baron, J. C. A. Janeway, and R. A. Flavell. Requirement for CD40 ligand in costimulation induction, T cell activation, and experimental allergic encephalomyelitis. Science. 1996. vol. 273: pp. 1864-1867.

Haneberg, B., D. Kendall, H. M. Amerongen, F. M. Apter, J. Kraehenbuhl, and M. R Neutra. Induction of specific immunoglobulin A in the small intestine, colon-rectum, and vagina measured by a new method for collection of secretions form local mucosal surfaces. Infection and Immunity. 1994. vol. 62, No. 1: pp. 152-23, by American Society for Microbiology.

Harding, F. A., and J. P. Allison. CD28-B7 interactions allow the induction of CD8+ cytotoxic T lymphocytes in the absence of exogenous help. The Journal of Experimental Medicine. 1993. vol. 177: pp. 1791-1796, by The Rockerfeller University Press.

Harlan, D. M., H. Hengartner, M. L. Huang, Y. H. Kang, R Abe, R W. Moreadith, H. Pircher, G. S. Gray, P. S. Ohashi, and G. J. Freeman. Mice expressing both B7-1 and viral glycoprotein on pancreatic beta cells along with glycoprotein-specific transgenic T cells develop diabetes due to a breakdown of T-lymphocyte unresponsiveness. Proceedings of the National Academy of Sciences USA. 1994. vol. 91: pp. 3137-3141.

Hathcock, K. S., G. Laszlo, C. Pucillo, P. Linsley, and R. J. Hodes. Comparative analysis of B7-1 and B7-2 costimulatory ligands: expression and function. The Journal of Experimental Medicine. 1994. vol. 180: pp. 631-640.

Hathcock, K. S., G. Laszlo, H. B. Dichler, J. Bradshaw, P. Linsley, and R. J. Hodes. Identification of an alternative CTLA- ligand costimulatory for T cell activation. Science. 1993. vol. 262: pp. 905-907.

Hochreiter, R., C. Ptaschinski, S. L. Kunkel, and R. Rochford. Murine gammaherpesvirus-68 productively infects immature dendritic cells and blocks maturation. Journal of General Virology. 2007. vol. 88: pp. 1896-1905, by SGM, Great Britain.

Hodge, J. W., J. P. McLaughlin, S. I. Abrams, W. L. Shupert, J. Schlom, and J. A. Kantor. Admixture of a recombinant vaccinia virus containing the gene for the costimulatory molecule B7 and a recombinant vaccinia virus containing a tumor-associated antigen gene results in enhanced specific T cell responses and antitumor immunity. Cancer Research. 1995. vol. 55: pp. 3598-3603.

Inaba, K., M. Witmer-Pack, M. Inaba, K. S. Hathcock, H. Sakuta, M. Azuma, H. Yagita, K. Okumura, P. S. Linsley, and S. Ikehara. The tissue distribution of the B7-2 costimulator in mice: abundant expression on dendritic cells in situ and during maturation in vitro. The Journal of Experimental Medicine. 1994. vol. 180: pp. 1849-1860.

Irie, H., Y. Harada, M. Kataoka, M. Nagamuta, Y. Moriya, M. Handa, M. Saito, S. Matsubara, K. Kojima, and Y. Sugawara. Efficacy of oral administration of live herpes simplex virus type 1 as a vaccine. Journal of Virology. 1992. vol. 66, No. 4: pp. 2428-2434, by American Society for Microbiology.

Janeway, C. A., Jr., and K. Bottomly. Signals and signs for lymphocyte responses. Cell. 1994. vol. 76: pp. 275-285, by Cell Press.

Jones, C. A., T. J. Taylor, and D. M. Knipe. Biological properties of herpes simplex virus 2 replication-defective mutant strains in a murine nasal infection model. Virology. 2000. vol. 278: pp. 137-150, by Academic Press.

Katz, J. P., E. T. Bodin, and D. M. Coen. Quantitative polymerase chain reaction analysis of herpes simplex virus DNA in ganglia of mice infected with replication-incompetent mutants. Journal of Virology. 1990. vol. 64, No. 9: pp. 4288-4295, by American Society for Microbiology.

Kaufman, H. L., G. Deraffele, J. Mitcham, D. Moroziewicz, S. M. Cohen, K. S. Hurst-Wicker, K. Cheung, D. S. Lee, J. Divito, M. Voulo, J. Donovan, K. Dolan, K. Manson, D. Panicali, E. Wang, H. Horig, and F. M. Marincola. Targeting the local tumor microenvironment with vaccinia virus expressing B7.1 for the treatment of melanoma. The Journal of Clinical Investigation. 2005. vol. 115, No. 7: pp. 1903-1912.

Kay, M. A., A.-X. Holterman, L. Meuse, A. Gown, H. D. Ochs, P. S. Linsley, and C. B. Wilson. Long-term hepatic adenovi.rus-mediated gene expression in mice following CTLA4Ig administration. Nature Genetics. 1995. vol. 11: pp. 191-197.

Keane-Myers, A. M., W. C. Gause, F. D. Finkelman, X. D. Xhou, and M. Wills-Karp. Development of murine allergic asthma is dependent upon B7-2 costimulation. The Journal of Immunology. 1998. vol. 160: pp. 1036-1043, by The American Association of Immunologists.

Knipe, D. M. and A. E. Spang. Definition of a series of stages in the association of two herpesviral proteins with the cell nucleus. Journal of Virology. 1982. vol. 43, No. 1: pp. 314-324.

Knipe, D. M., X. DaCosta, L. A. Morrison, N. Bourne, and L. R Stanberry. Immunization against genital herpes disease with a replication-defective mutant of herpes simplex virus 2. Cold Spring Harbor Laboratory Press, Plainview. In: Vaccines 95: pp. 369-374. Copyright 1995.

Koelle, D. M., L. Corey, R L. Burke, R. J. Eisenberg, G. H. Cohen, R. Pichyangkura, and S. J. Triezenberg. Antigenic specificities of human CD4-30 T-cell clones recovered from recurrent genital herpes simplex virus type 2 lesions. Journal of Virology. 1994. vol. 68, No. 5: pp. 2803-2810, by American Society for Microbiology.

Kolaitis, G., M. Doymaz, and B. T. Rouse. Demonstration of MHC class II-restricted cytotoxic T lymphocytes in mice against herpes simplex virus. Immunology. 1990. vol. 71: pp. 101-106.

Kuchroo, V. K., M. P. Das, J. A. Brown, A. M. Ranger, S. S. Zamvil, R. A. Sobel, H. L. Weiner, N. Nabavia, and L. H. Glimcher. B7-1 and B7-2 costimulatory molecules activate differentially the Th1/Th2 developmental pathways: application to autoimmune disease therapy. Cell. 1995. vol. 80: pp. 707-718 by Cell Press.

Kuper, C. F., P, J. Koornstra, D. M. H. Hameleers, J. Biewenga, B. J. Spit, A. M. Duijvestijn, P. J. van Breda Vriesman, and T. Sminia. The role of nasopharyngeal lymphoid tissue. Immunology Today. 1991. vol. 13, No. 6: pp. 219-224, by Elsevier Science Publishers Ltd, UK.

Kwong, A. D. and N. Frenkel. Herpes simplex virus-infected cells contain a function(s) that destabilizes both host and viral mRNAs. Porceedings of the National Academy of Sciences USA. 1987. vol. 84: pp. 1926-1930, by Cell Biology.

Lanier, L., S. O'Fallon, C. Somoza, J. Phillips, P. Linsley, K. Okumura, D. Ito, and M. Azuma. CD80 (B7) and CD86 (B70) provide similar costimulatory signals for T cell proliferation, cytokine production, and generation of CTL. The Journal of Immunology. 1995. vol. 154: pp. 97-105, by The American Association of Immunologists.

Lee, Y. S., J. H. Kim, K. J. Choi, I. K. Choi, H. Kim, S. Cho, B. C. Cho, and C. O. Yun. Enhanced antitumor effect of oncolytic adenovirus expressing interleukin-12 and B7-1 in an immunocompetent murine model. Clinical Cancer Research. 2006. vol. 12, No. 19: pp. 5859-5868, by American Association for Cancer Research.

Lenschow, D. J., A. I. Sperling, G. J. Cooke, G. J. Freeman, L. Rhee, and D. C. Decker. Differential up-reguation of the B7-1 and B7-2 costimulatory molecules after Ig receptor engagement by antigen. The Journal of Immunology. 1994. vol. 153: pp. 1990-1997, by The American Association of Immunologists.

Lenschow, D. J., S. C. Ho, H. Sattar, L. Rhee, G. Gray, N. Nabavi, K. C. Herold, and J. A. Bluestone. Differential effects of anti-B7-1 and anti-B7-2 monoclonal antibody treatment on the development of diabetes in the nonobese diabetic mouse. The Journal of Experimental Medicine. 1995. vol. 181: pp. 1145-1155, by the Rockefeller University Press.

Levine, B. L., Y. Ueda, N. Craighead, M. L. Huang, and C. H. June. CD28 ligands CD80 (B7-1) and CD86 (B7-2) induce long-term autocrine growth of CD4+ T cells and induce similar patterns of cytokine secretion in vitro. International Immunology. 1995. vol. 7, No. 6: pp. 891-904.

Linsley, P. S., W. Brady, L. Grosmaire, A. Aruffo, N. K. Damle, and J. A. Ledbetter. Binding of the B cell activation antigen B7 to CD28 costimulates T cell proliferation and interleukin 2 mRNA accumulation. The Journal of Experimental Medicine. 1991. vol. 173: pp. 721-730, by the Rockefeller University Press.

Liu, T., Q. Tang, and R L. Hendricks. Inflammatory infiltration of the trigeminal ganglion after herpes simplex virus type 1 corneal infection. Journal of Virology. 1996. vol. 70, No. 1: pp. 264-271, by American Society for Microbiology.

Lumsden, J., J. Roberts, N. Harris, R. Peach, and F. Ronchese. Differential requirement for CD80 and CD80/CD86-dependent costimulation in the lung immune response to an influenza virus infection. The Journal of Immunology. 2000. vol. 164: pp. 79-85, by The American Association of Immunologists, Inc.

Manickan, E. and B. T. Rouse. Roles of different T-cell subsets in control of herpes simplex virus infection determined by using T-cell-deficient mouse models. Journal of Virology. 1995. vol. 69, No. 12: pp. 8178-8179, by American Society for Microbiology.

Margolis, T. P., C. R. Dawson, and J. H. LaVail. Herpes simplex viral infection of the mouse trigeminal ganglion Immunohistochemical analysis of cell populations. Investigative Ophthalmology & Visual Science. 1992. vol. 33/2: pp. 259-267.

Marti, W. R, D. Oertli, J. B. Meko, J. A. Norton, and K. Tsung. Induction of antigen-presenting capacity in tumor cells upon infection with non-replicating recombinant vaccinia virus encoding murine MHC class II and costimulatory molecules. Journal of Immunological Methods. 1997. vol. 200: pp. 191-198, by Elsevier Science B.V.

Marti, W. R., P. Zajac, G. Spagnoli, M. Heberer, and D. Oertli. Nonreplicating recombinant vaccinia virus encoding human B-7 molecules elicits effective costimulation of naive and memory CD4+ T lymphocytes in vitro. Cellular Immunology. 1997. vol. 179: pp. 146-152, by Academic Press.

Matloubian, M., R. J. Concepcion, and R. Ahmed. CD4+ T cells are required to sustain CDB+ cytotoxic T-cell responses during chronic viral infection. Journal of Virology. 1994. vol. 68, No. 12: pp. 8056-8063, by American Society for Microbiology.

Maue, A. C., W. R. Waters, M. V. Palmer, D. L. Whipple, F. C. Minion, W. C. Brown, and D. M. Estes. CD80 and CD86, but not CD154, augment DNA vaccine-induced protection in experimental bovine tuberculosis. Vaccine. 2004. vol. 23: pp. 769-779, by Elsevier Ltd.

McAdam, A. J., E. A. Farkash, B. E. Gewurz, and A. H. Sharpe. B7 costimulation is critical for antibody class switching and CD8(+) cytotoxic T-lymphocyte generation in the host response to vesicular stomatitis virus. Journal of Virology. 2000. vol. 74, No. 1: pp. 203-208, by American Society for Microbiology.

McDermott, M. R, C. H. Goldsmith, K. L. Rosenthal, and L. J. Brais. T lymphocytes in genital lymph nodes protect mice from intravaginal infection with herpes simplex virus type 2. The Journal of Infectious Diseases. 1989. vol. 159, No. 3: pp. 460-466, by The University of Chicago.

McDermott, M. R., J. R. Smiley, P. Leslie, J. Brais, H. E. Rudzroga, and J. Bienenstock. Immunity in the female genital tract after intravaginal vaccination of mice with an attenuated strain of herpes simplex virus type 2. Journal of Virology. 1984. vol. 51, No. 3: pp. 747-753, by American Society for Microbiology.

McGhee, J. R. and H. Kiyono. New perspectives in vaccine development: mucosal immunity to infections. Infectious Agents and Disease. 1993. vol. 2: pp. 55-73, by Raven Press, Ltd., New York.

McGhee, J. R., J. Xu-Amano, C. J. Miller, R. J. Jackson, K. Fujihashi, H. F. Staats, and H. Kiyono. The common mucosal immune system: from basic principles to enteric vaccines with relevance for the female reproductive tract. Reproduction, Fertility and Development. 1994. vol. 6: pp. 369-379.

McLean, C. S., D. Ni Challanain, L Duncan, M. E. G. Boursnell, R. Jennings, and S. C. Inglis. Induction of a protective immune response by mucosal vaccination with a DISC HSV-1 vaccixte. Vaccine. 1996. vol. 14, No. 10: pp. 987-992, by Elsevier Science Ltd., Great Britain.

McLean, C. S., M. Erturk, R Jennings, D. Ni Challanain, A. C. Minson, I. Duncan, M. E. G. Boursnell, and S. C. Inglis. Protective vaccination against primary and recurrent disease caused by herpes simplex virus (HSV) type 2 using a genetically disabled HSV-1. The Journal of Infectious Diseases. 1994. vol. 170: pp. 1100-1109, by The University of Chicago.

Milligan, G. N. and D. L Bernstein. Analysis of herpes simplex virus-specific T cells in the murine female genital tract following genital infection with herpes simplex virus type 2. Virology. 1995. vol. 212: pp. 481-489, by Academic Press, Inc.

Mintern, J. D., E. J. Klemm, M. Wagner, M. E. Paquet, M. D. Napier, Y. M. Kim, U. H. Koszinowski, and H. L. Ploegh. Viral interference with B7-1 costimulation: a new role for murine cytomegalovirus Fc receptor-1. The Journal of Immunology. 2006. vol. 177: pp. 8422-8431, by The American Association of Immunologists, Inc.

Morrison LA, L Zhu, and LG Thebeau. Vaccine-induced serum immunoglobin contributes to protection from herpes simplex virus type 2 genital infection in the presence of immune T cells. Journal of Virology. 2001. vol. 75, No. 3: pp. 1195-1204, by American Society for Microbiology.

Morrison, L. A. and D. M. Knipe. Immunization with replication-defective mutants of herpes simplex virus type 1: Sites of immune intervention in pathogenesis of challenge virus infection. Journal of Virology. 1994. vol. 68, No. 2: pp. 689-696, by American Society for Microbiology.

Morrison, L. A. and D. M. Knipe. Mechanisms of immunization with a replication-defective mutant of herpes simplex virus 1. Virology. 1996. vol. 220: pp. 402-413, by Academic Press, Inc.

Morrison, L. A., V. L. Braciale, and T. J. Braciale. Antigen form determines induction and frequency of influenza-specific class I and class II MHC-restricted cytolytic T lymphocytes. The Journal of Immunology. 1988. vol. 141, No. 2: pp. 363-368, by The American Association of Immunologists.

Morrison, L. A., X. J. Da Costa, and D. M. Knipe. Influence of mucosal and parenteral immunization with a replication-defective mutant of HSV-2 on immune responses and protection from genital challenge. Virology. 1998. vol. 243: pp. 178-187, by Academic Press.

Mosmann, T. R. and R. L. Coffman. Th1 and Th2 cells: Different patterns of lymphokine secretion lead to different functional properties. Annual Review of Immunology. 1989. vol. 7: pp. 145-173, by Annual Reviews Inc.

Murphy, K 1VL, A.1VL Heimberger, and D. Y. Loh. Induction by antigen of intrathymic apoptosis of CD4+, CD8+, TCRIo thymocytes in vivo. Science. 1990. vol. 250: pp. 1720-1723.

Murphy, M. L., C. R. Engwerda, P. M. Gorak, and P. M. Kaye. B7-2 blockade enhances T cell responses to *Leishmania donovani*. The Journal of Immunology. 1997. vol. 159: pp. 4460-4466, by The American Association of Immunologists.

Nash, A. A., A. Jayasuriya, J. Phelan, S. P. Cobbold, H. Waldmann, and T. Prospero. Different roles for L3T4+ and Lyt 2+ T cell subsets in the control of an acute herpes simplex virus infection of the skin and nervous system. Journal of General Virology. 1987. vol. 68: pp. 825-833, by SGM, Great Britain.

Nasir, A., B. Ferbel, W. Salminen, R. K. Barth, and A. A. Gaspari. Exaggerated and persistent cutaneous delayed-type hypersensitivity in transgenic mice whose epidermal keratinocytes constitutively express B7-1 antigen. The Journal of Clinical Investigation. 1994. vol. 94: pp. 892-898, by The American Society for clinical Investigation, Inc.

Natesan, M., Z. Razi-Wolf, and H. Reiser. Costimulation of IL-4 production by murine B7-1 and B7-2 molecules. The Journal of Immunology. 1996. vol. 156: pp. 2783-2791, by The American Association of Immunologists.

Nguyen, L. H., D.1VL Knipe, and R W. Finberg. Replication-defective mutants of herpes simplex virus (HSV) induce cellular immunity and protect against lethal HSV infection. Journal of Virology. 1992. vol. 66, No. 12: pp. 7067-7072 by American Society for Microbiology.

Nguyen, L., D. M. Knipe, and R. W. Finberg. Mechanism of virus-induced Ig subclass shifts. The Journal of Immunology. 1994. vol. 152: pp. 478-484, by the American Association of Immunologists.

Novak, M., M. Yamamoto, K. Fujihashi, Z. Moldoveanu, H. Kiyono, J. R. McGhee, and J. Mestecky. Ig-secreting and interferon-gamma-producing cells in mice mucosally immunized with influenza virus. Advances in Mucosal Immunology. 1995: pp. 1587-1590, by Plenum Press, New York.

Nowak, R. New push to reduce material mortality in poor countries. Science. 1995. vol. 269: pp. 780-782.

Milligan, G. N. and D. L Bernstein. Generation of humoral immune responses against herpes simplex virus type 2 in the murine female genital tract. Virology. 1995. vol. 206: pp. 234-241, by Academic Press, Inc.

Oertli, D., W. R. Marti, J. A. Norton, and K. Tsung. Non-replicating recombinant vaccinia virus encoding murine B-7 molecules elicits effective costimulation of naive CD4 (+) splenocytes in vitro. Journal of General Virology. 1996. vol. 77: pp. 3121-3125.

Okahashi, N., M. Yamamoto, J. L. VanCott, S. N. Chatfield, M. Roberts, H. Bluethmann, T. Hiroi, H. Kivono, and J. R. McGhee. Oral immunization of interleukin-4 (IL-4) knockout mice with a recombinant *Salmonella* strain or cholera toxin reveals that CD4+ Th2 cells producing 11.-6 and IL-10 are associated with mucosal immunoglobulin A responses. Infection and Immunity. 1996. vol. 64, No. 5: pp. 1516-1525, by American Society for Microbiology.

Osorio Y, Cai S, Ghiasi H. Treatment of mice with anti-CD86 mAb reduces CD8+ T cell-mediated CTL activity and enhances ocular viral replication in HSV-1-infected mice. Ocular Immunology and Inflammation. 2005. vol. 13: pp. 159-167, by Taylor & Francis Inc.

Parr, M. B., L. Kepple, M. R. McDermott, M. D. Drew, J. J. Bozzola, and E. L. Parr. A mouse model for studies of mucosal immunity to vaginal infection by herpes simplex virus type 2. Laboratory Investigation. 1994. vol. 70, No. 3: pp. 369-380, by The United States and Canadian Academy of Pathology, Inc.

Paul, W. E. and R A. Seder. Lymphocyte responses and cytokines. Cell. 1994. vol. 76: pp. 241-251, by Cell Press.

Petrulio, C. A., and H. L. Kaufman. Development of the PANVAC-VF vaccine for pancreatic cancer. Expert Review of Vaccines. 2006. vol. 5, No. 1: pp. 9-19, by Future Drugs Ltd.

Posavad, C. M., D. M. Koelle, and L. Corey. High frequenccy of CD8+ cytotoxic T-lymphocyte precursors specific for herpes simplex viruses in persons with genital herpes. Journal of Virology. 1996. vol. 70, No. 11: pp. 8165-8168, by American Society for Microbiology.

Ramsay, A. J., A. J. Husband, L A. Ramsbaw, S. Bao, K. L Matthaei, G. Koehler, and M. Kopf. The role of interleukin-6 in mucosal IgA antibody responses in vivo. Science. 1994. vol. 264: pp. 561-563.

Ranger, A. M., M. P. Das, V. K. Kuichroo, and L. H. Glimcher. B7-2 (CD86) is essential for the development of IL-4-producing T cells. International Immunology. 1996. vol. 8, No. 10: pp. 1549-1560, by Oxford University Press.

Rooney, J. F., C. Wohlenberg, K. J. Cremer, B. Moss, and A. L. Notkins. Immunization with a vaccinia virus recombinant expressing herpes simplex virus type 1 glycoprotein D: long-term protection and effect of revaccination. Journal of Virology. 1988. vol. 62, No. 5: pp. 1530-1534.

Rouse, R J., S. K. Nair, S. L. Lydy, J. C. Bowen, and B. T. Rouse. Induction in vitro of primary cytotoxic T-lymphocyte responses with DNA encoding herpes simplex virus. Journal of Virology. 1994. vol. 68, No. 9: pp. 5685-5689, by American Society for Microbiology.

Ruyechan, W. T., L. S. Morse, D. M. Knipe, and B. Roisman. Molecular genetics of herpes simplex virus. Mapping of the major viral glycoproteins and of the genetic loci specifying the social behavior of infected cells. Journal of Virology. 1979. vol. 29, No. 2: pp. 677-697.

Charders, T., F. Velge-Roussel, P. Mevelec, M. N. Mevelec, D. Buzoni-Gatel, and D. Bout. Mucosal and systemic cellular immune responses induced by *Toxoplamsa gondii* antigens in cyst orally infected mice. Immunology. 1993. vol. 78: pp. 421-429.

Salio, M., M. Cella, M. Suter, and A. Lanzavecchia. Inhibition of dendritic cell maturation by herpes simplex virus. European Journal of Immunology. 1999. vol. 29: pp. 3245-3253, by Wiley-VCH Verlag GmbH, D-69451 Weinheim.

Samady, L., E. Costigliola, L. MacCormac, Y. McGrath, S. Cleverley, C. E. Lilley, J. Smith, D. S. Latchman, B. Chain, and R. S. Coffin. Deletion of the virion host shutoff protein (vhs) from herpes simplex virus (HSV) relieves the viral block to dendritic cell activation: potential of vhs-HSV vectors for dendritic cell-mediated immunotherapy. Journal of Virology. 2003. vol. 77, No. 6: pp. 3768-3776, by American Society for Microbiology.

Santra, S., D. H. Barouch, S. S. Jackson, M. J. Kuroda, J. E. Schmitz, M. A. Lifton, A. H. Sharpe, and N. L. Letvin. Functional equivalency of B7-1 and B7-2 for costimulating plasmid DNA vaccine-elicited CTL responses. The Journal of Immunology. 2000. vol. 165: pp. 6791-6795, by The American Association of Immunologists, Inc.

Schmidt, D. S., A. M. Eis-Hubinger, and K. E. Schneweis. The role of the immune system in establishment of herpes simplex virus latency-studies using CD4+ T-cell depleted mice. Archives of Virology. 1993. vol. 133: pp. 179-187, by Springer-Verlag.

Schreiber, R D. Measurement of Mouse and Human Interferon gamma. Current Protocols in Immunology vol. 1: pp. 6.8.1-6.8.8, by Current Protocols.

Schweitzer, A. N., F. Borriello, R. C. Wong, A. K. Abbas, and A. H. Sharpe. Role of costimulators in T cell differentiation: studies using antigen-presenting cells lacking expression of CD80 or CD86. The Journal of Immunology. 1997. vol. 158: pp. 2713-2722, by The American Association of Immunologists.

Schweitzer, A., and A. Sharpe. Studies using antigen-presenting cells lacking expression of both B7-1 (CD80) and B7-2 (CD86) show distinct requirements for B7 molecules during priming versus restimulation of Th2 but not Th1 cytokine production. The Journal of Immunology. 1998. vol. 161: pp. 2762-2771, by The American Association of Immunologists.

Shahinian, A., K. Pfeffer, K. P. Lee, T. M. Kundig, K. Kishihara, A. Wakeham, K. Kawai, P. S. Ohashi, C. B. Thompson, and T. W. Mak. Differential T cell costimulatory requirements in CD28-deficient mice. Science. 1993. vol. 261: pp. 609-612.

Sharpe, A. H., and G. J. Freeman. The B7-CD28 superfamily. Nature Reviews Immunology. 2002. vol. 2: pp. 116-126, by Macmillan Magazines Ltd.

Showalter, S. D., M. Zwieg, and B. Hampar, Monoclonal antibodies to herpes simplex virus type 1 proteins, including the immediate-early protein ICP 4. Infection and Immunity. 1981. vol. 34, No. 3: pp. 684-692.

Sigal, L. J., H. Reiser, and K. L. Rock. The role of B7-1 and B7-2 costimulation for the generation of CTL responses in vivo. The Journal of Immunology. 1998. vol. 161: pp. 2740-2745, by The American Association of Immunologists, Inc.

Simmons, A. and D. C. Tscharke. Anti-CD8 impairs clearance of herpes simplex virus from the nervous system: implications for the fate of virally infected neurons. The Journal of Experimental Medicine. 1992. vol. 175: pp. 1337-1344, by The Rockefeller University Press.

Smith, T. J., L. A. Morrison, and D. A. Leib. Pathogenesis of herpes simplex virus type 2 virion host shutoff (vhs) mutants. Journal of Virology. 2002. vol. 76, No. 5: pp. 2054-2061, by American Society for Microbiology.

Spang, A. E., P. J. Godowski, and D. M. Knipe. Characterization of herpes simplex virus 2 temperature-sensitive mutants whose lesions map in or near the coding sequences for the major DNA-binding protein. Journal of Virology. 1983. vol. 45, No. 1: pp. 332-342, by American Society for Microbiology.

Strelow, L. I. and D. A. Leib. Role of the virion host shutoff (vhs) of herpes simplex virus type 1 in latency and pathogenesis. Journal of Virology. 1995. vol. 69, No. 11: pp. 6779-6786, by American Society for Microbiology.

Strom, T. and N. Frenkel. Effects of herpes simplex virus on mRNA stability. Journal of Virology. 1987. vol. 61, No. 7: pp. 2198-2207, by American Society for Microbiology.

Suresh, M., J. K. Whitmire, L. E. Harrington, C. P. Larsen, T. C. Pearson, J. D. Altman, and R. Ahmed. Role of CD28-B7 interactions in generation and maintenance of CD8 T cell memory. The Journal of Immunology. 2001. vol. 167: pp. 5565-5573, by The American Association of Immunologists, Inc.

Thapar, M. A., E. L. Parr, and M. B. Parr. Secretory immune responses in mouse vaginal fluid after pelvic, parenteral or vaginal immunization. Immunology. 1990. vol. 70: pp. 121-125.

Thebeau, L. G., and L. A. Morrison. B7 costimulation plays an important role in protection from herpes simplex virus type 2-mediated pathology. Journal of Virology. 2002. vol. 76, No. 5: pp. 2563-2566, by American Society for Microbiology.

Thebeau, L. G., and L. A. Morrison. Mechanism of reduced T-cell effector functions and class-switched antibody responses to herpes simplex virus type 2 in the absence of B7 costimulation. Journal of Virology. 2003. vol. 77, No. 4: pp. 2426-2435, by American Society for Microbiology.

Thompson, C. B. Distinct roles for the costimulatory ligands B7-1 and B7-2 in T helper cell differentiation? Cell. 1995. vol. 81: pp. 979-982, by Cell Press.

Todo, T., R. L. Martuza, M. J. Dallman, and S. D. Rabkin. In situ expression of soluble B7-1 in the context of oncolytic herpes simplex virus induces potent antitumor immunity. Cancer Research. 2001. vol. 61: pp. 153-161.

Tomoda, T., H. Morita, T. Kurashige, and H. F. Maassab. Prevention of influenza by the intranasal administration of cold-recombinant, live-attenuated influenza virus vaccine: importance of interferon-gamma production and local IgA response. Vaccine. 1995. vol. 13, No. 2: pp. 185-190, by Elsevier Science Ltd.

Tsuji, T., K. Hamajima, N. Ishii, I. Aoki, J. Fukushima, K. Q. Xin, S. Kawamoto, S. Sasaki, K. Matsunaga, Y. Ishigatsubo, K. Tani, T. Okubo, and K. Okuda. Immunomodulatory effects of a plasmid expressing B7-2 on human immunodeficiency virus-1-specific cell-mediated immunity induced by a plasmid encoding the viral antigen. European Journal of Immunology. 1997. vol. 27: pp. 782-787, by VCH Verlagsgesellschaft mbH, D-69451 Weinheim.

Vajdy, M., M. H. Kosco-Vilbois, M. Kopf, G. Kdhler, and N. Lycke. Impaired mucosal immune responses in interleukin 4-targeted mice. The Journal of Experimental Medicine. 1995. vol. 181: pp. 41-53, by The Rockefeller University Press.

van der Ven, I. and T. Sminia. The development and structure of mouse nasal-associated lymphoid tissue: An immuno- and enzyme-histochemical study. Regional Immunology. 1993. vol. 5: pp. 69-75, by John Wiley & Sons, Inc.

VanCott, J. L., R Jackson, M. Yamamoto, F. W. van Ginkel, N. Okahashi, M. Marinaro, J. R McGhee, and H. Kiyono. Optimization of mucosal vaccine delivery systems for the induction of mucosal and systemic immune responses and advances in detection of mucosal antibodies. Vaccines. 1996. vol. 96: pp. 169-175, by Cold Spring Harbor Laboratory Press.

Walboomers, J. M. and J. T. Schegget. A new method for the isolation of herpes simplex virus type 2 DNA. Virology. 1976. vol. 74: pp. 256-258, by Academic Press, Inc.

Waldo, F. B., A. W. van den Wall Bake, J. Mestecky, and S. Husby. Suppression of the immune response by nasal immunization. Clinical Immunology and Immunopathology. 1994. vol. 72, No. 1: pp. 30-34, by Academic Press, Inc.

Whitley, R. J. Herpes simplex viruses. Fields Virology. 1996. 3rd edition: pp. 2297-2342, by Lippincott-Raven Publishers, Philadelphia.

Williams, L R, R J. Ort, and T. S. Kupper. Keratinocyte expression of B7-1 in transgenic mice amplifies the primary immune response to cutaneous antigens. Proceedings of the National Academy of Sciences USA. 1994. vol. 91: pp. 12780-12784.

Wu, Z. Q., A. Q. Khan, Y. Shen, J. Schartman, R. Peach, A. Lees, J. J. Mond, W. C. Gause, and C. M. Snapper. B7 requirements for primary and secondary protein- and polysaccharide-specific Ig isotype responses to *Streptococcus pneumoniae*. The Journal of Immunology. 2000. vol. 165: pp. 6840-6948, by The American Association of Immunologists.

Yamamoto, M., J. L. VanCott, N. Okahashi, M. Marinaro, H. Kiyono, K. Fujihashi, R J. Jackson, S. N. Chatfield, H. Bluethmann, and J. R McGhee. The role of Th1 and Th2 cells for mucosal IgA responses. Annals of the New York Academy of Sciences. 2006. vol. 778, No. 1: pp. 64-71, by The New York Academy of Sciences.

Yang, Y. and J. M. Wilson. CD40 Ligand-dependent T cell activation: requirement of B7-CD28 signaling through CD40. Science. 1996. vol. 273: pp. 1862-1864.

Zajac, P., A. Schutz, D. Oertli, C. Noppen, C. Schaefer, M. Heberer, G. C. Spagnoli, and W. R. Marti. Enhanced generation of cytotoxic T lymphocytes using recombinant vaccinia virus expressing human tumor-associated antigens and B7 costimulatory molecules. Cancer Research. 1998. vol. 58: pp. 4567-4571.

Zarling, J. M., P. A. Moran, L. A. Lasky, and B. Moss. Herpes simplex virus (HSV)-specific human T-cell clones recognize HSV glycoprotein D expressed by a recombinant vaccinia virus. Journal of Virology. 1986. vol. 59, No. 2: pp. 506-509, by American Society for Microbiology.

Zhao, X., E. Deak, K. Soderberg, M. Linehan, D. Spezzano, J. Zhu, D. M. Knipe, and A. Iwasaki. Vaginal submucosal dendritic cells, but not Langerhans cells, induce protective Th1 responses to herpes simplex virus-2. The Journal of Experimental Medicare. 2003. vol. 197, No. 2: pp. 153-162, by The Rockerfeller University Press.

Zheng, J., L. Si, J. Song, X. Sun, J. Yu, and Y. Wang. Enhanced immune response to DNA-based HPV16L1 vaccination by costimulatory molecule B7-2. Antiviral Research. 2003. vol. 59: pp. 61-65, by Elsevier Science B.V.

Zimmermann, C., P. Seiler, P. Lane, and R M. Zinkernagel. Antiviral immune responses in CTLA4 transgenic mice. Journal of Virology. 1997. vol. 71, No. 3: pp. 1802-1807, by American Society for Microbiology.

Zollinger, W. D. and J. W. Boslego. A general approach to standardization of the solid-phase radioimmunoassay for quantitation of class-specific antibodies. Journal of Immunological Methods. 1981. vol. 46: pp. 129-140, by Elsevier North-Holland Biomedical Press.

Second Declaration of Dr. Lynda A. Morrison, Jun. 2, 2011.

Hunter et al., "Attenuated, Replication-Competent Herpes Simplex Virus Type 1 Mutant G207: Safety Evaluation of Intracerebral Injection in Nonhuman Primates", *Journal of Virology*, vol. 73(8), pp. 6319-6326, (Aug. 1999).

Todo et al., "Oncolytic Herpes Simplex Virus Vector with Enhanced MHC Class I Presentation and Tumor Cell Killing", *PNAS*, vol. 98(11), pp. 6996-6401 (May 22, 2001).

Todo et al., "Systemic Antitumor Immunity in Experimental Brain Tumor Therapy Using a Multimutated, Replication-competent Herpes Simplex Virus", *Hum Gene Ther.*, 10(17), pp. 2741-2755 (Nov. 20, 1999).

Hunter, et al., "Attenuated, Replication-Competent Herpes Simplex Virus Type 1 Mutant G207: Safety Evaluation of Intracerebral Injection in Nonhuman Primates", Journal of Virology, vol. 73(8), pp. 6319-6326 (Aug. 1999).

Todo, et al., "Oncolytic Herpes Simplex Virus Vector with Enhanced MHC Class I Presentation and Tumor Cell Killing", PNAS, vol. 98 (11), pp. 6396-6401 (May 22, 2001).

Todo, et al., "Systemic Antitumor Immunity in Experimental Brain Tumor Therapy Using a Multimutated, Replication-competent Herpes Simplex Virus", Hum Gene Ther., 10(17), pp. 2741-2755, Nov. 20, 1999.

Boss et al., *Blood*, vol. 56(5), pp. 910-916 (Nov. 1980).

Majeti, *Oncogene*, vol. 30, pp. 1009-1019 (2011).

Pesando et al., *J. Immunol.*, vol. 136(7), pp. 2709-2714 (Apr. 1986).

Bennett et al., *Cecil Textbook of Medicine*, vol. 2(20), pp. 1770-1774 (1996).

Greenwald et al., *Annu. Rev. Immunol.*, vol. 23, pp. 515-548 (Jan. 2005).

Strand, et al., The Virion Host Shutoff Protein of Herpes Simplex Virus Type 1 Has RNA Degradation Activity in Primary Neurons; Journal of Virology, 2004, vol. 78, No. 15, pp. 8400-8403.

Everly, Jr. et al., Site-Directed Mutagenesis of the Virion Host Shutoff Gene (UL41) of Herpes Simplex Virus (HSV): Analysis of Functional Differences Between HSV Type 1 (HSV-1) and HSV-2 Alleles; Journal of Virology; 1999, vol. 73, No. 11, pp. 9117-9129.

Tigges, et al., Human Herpes Simplex Virus (HSV)-Specific CD8+ CTL Clones Recognize HSV-2 Infected Fibroblasts After Treatment with IFN-y or When Virion Host Shutoff Functions are Disabled; Journal of Immunology, 1996, vol. 156, pp. 3901-3910.

Trgovcich, et al., Cell Surface Major Histocompatibility Complex Class II Proteins Are Regulated by the Products of the y134.5 and UI41 Genes of Herpes Simplex Virus 1; Journal of Virology; 2002; vol. 76, No. 14; pp. 6974-6986.

Harris, et al., The Role of B7 Costimulation in T-cell Immunity; Immunology and Cell Biology; 1999; vol. 77; pp. 304-311.

* cited by examiner

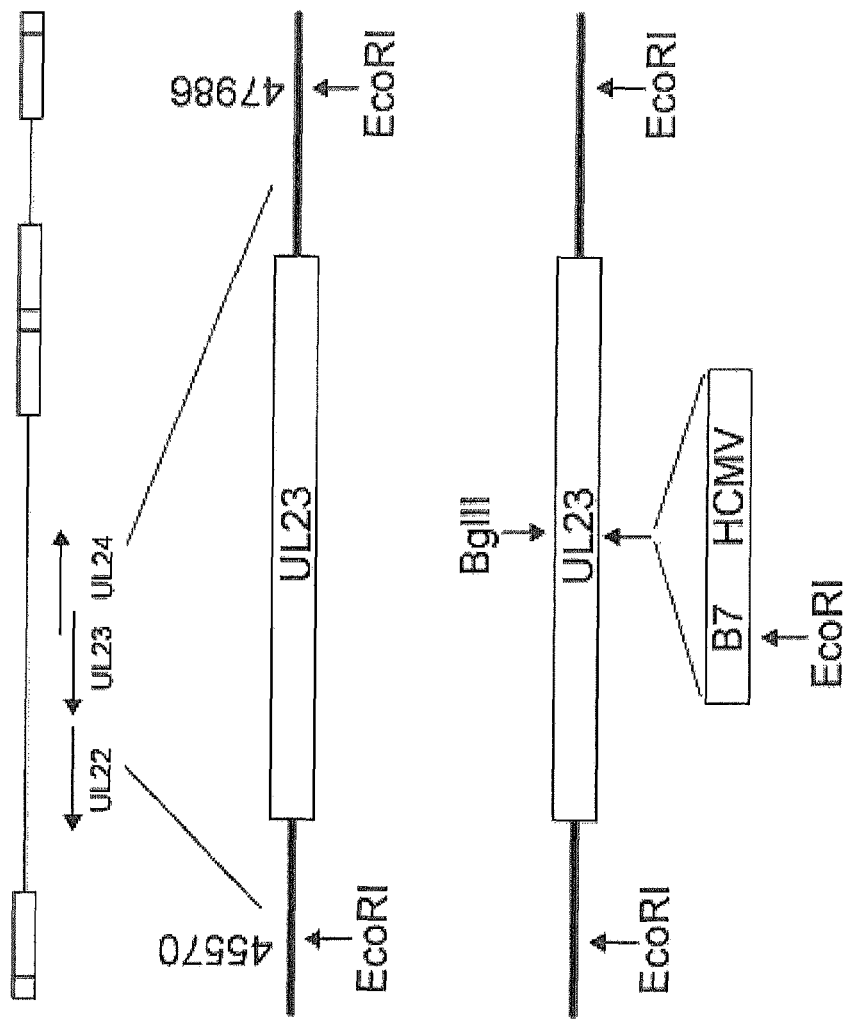

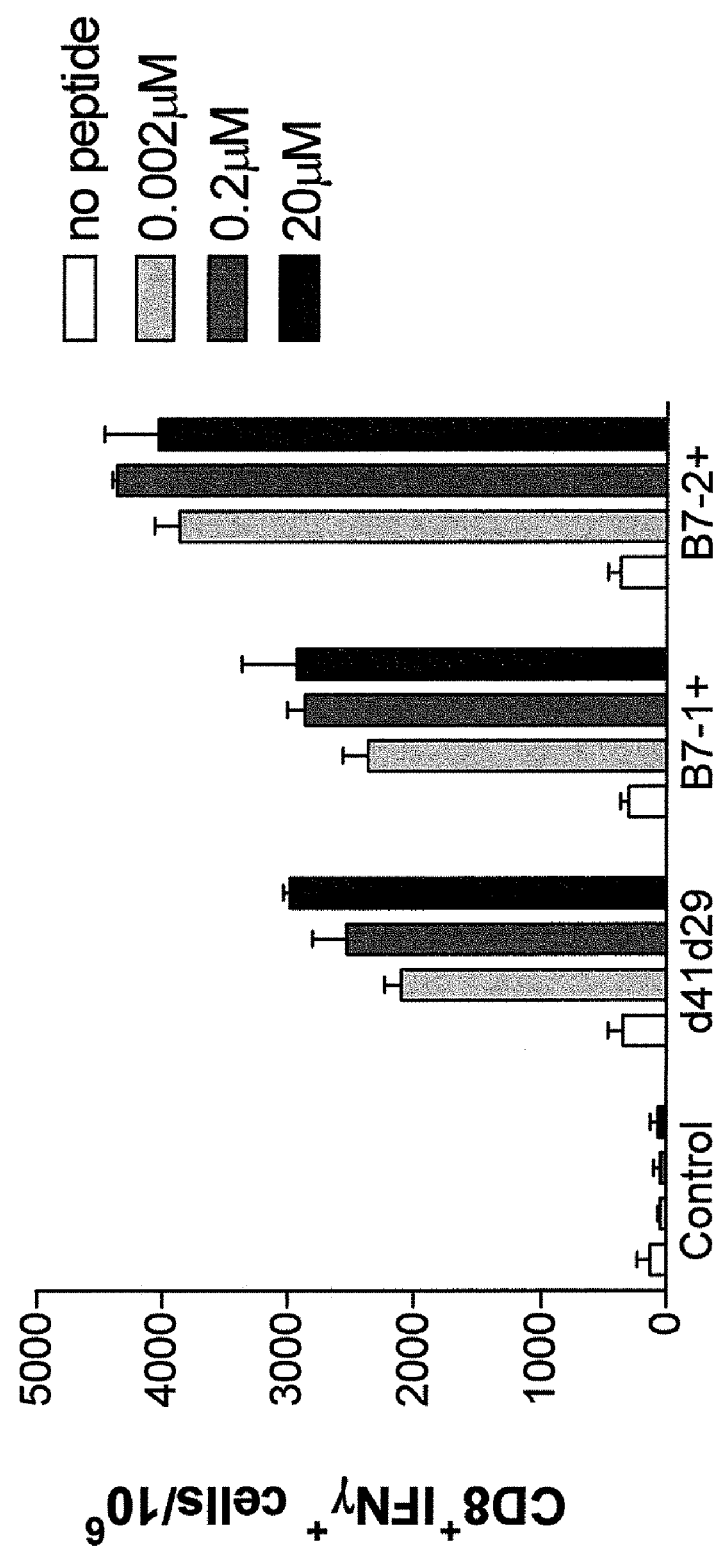

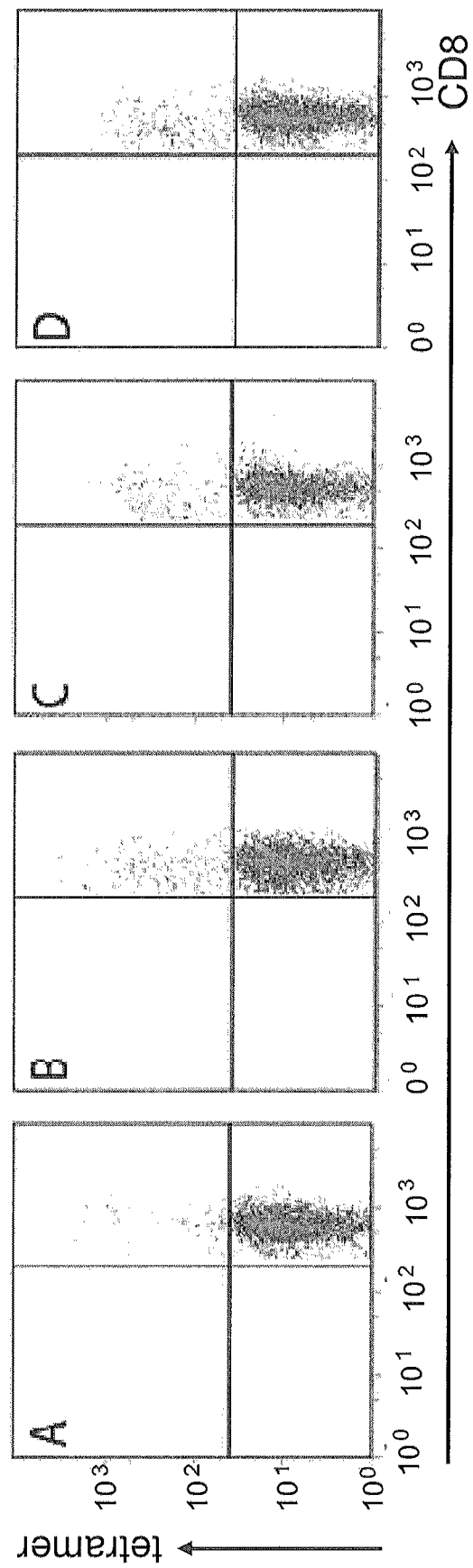

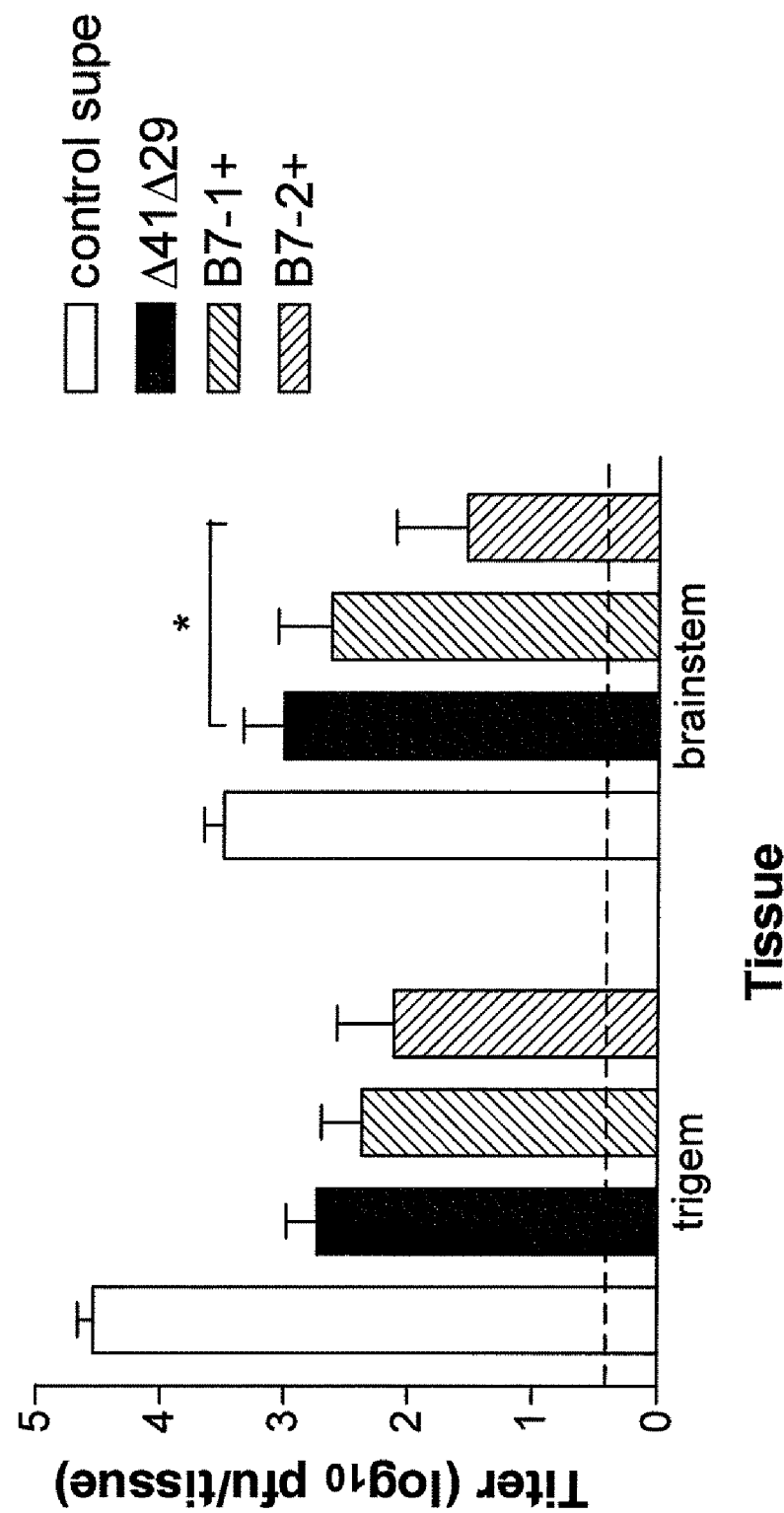

VIRUS-EXPRESSING HOST COSTIMULATION MOLECULES

CROSS-REFERENCE TO RELATED APPLICATIONS

Figure 2:
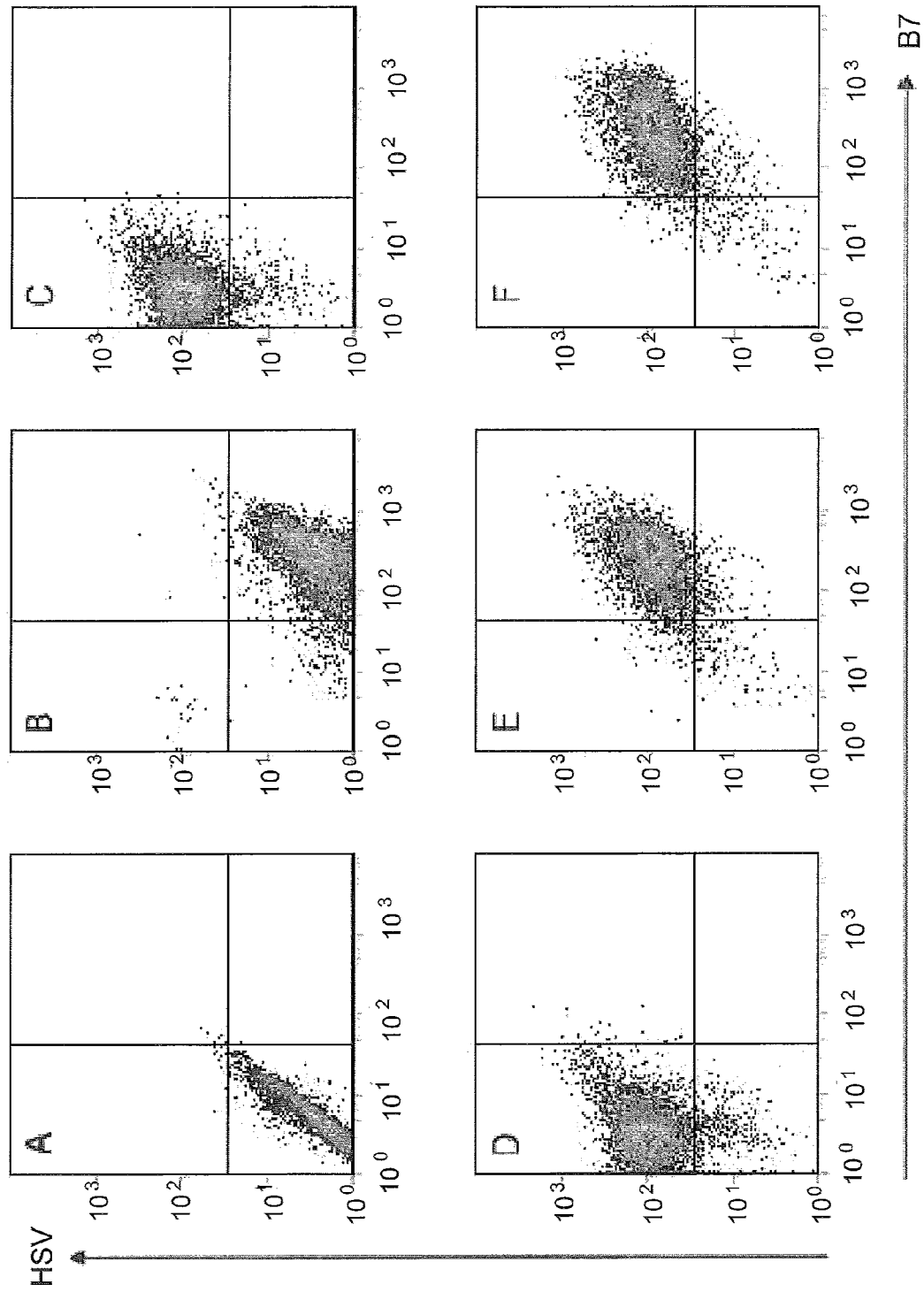
Figure 4:
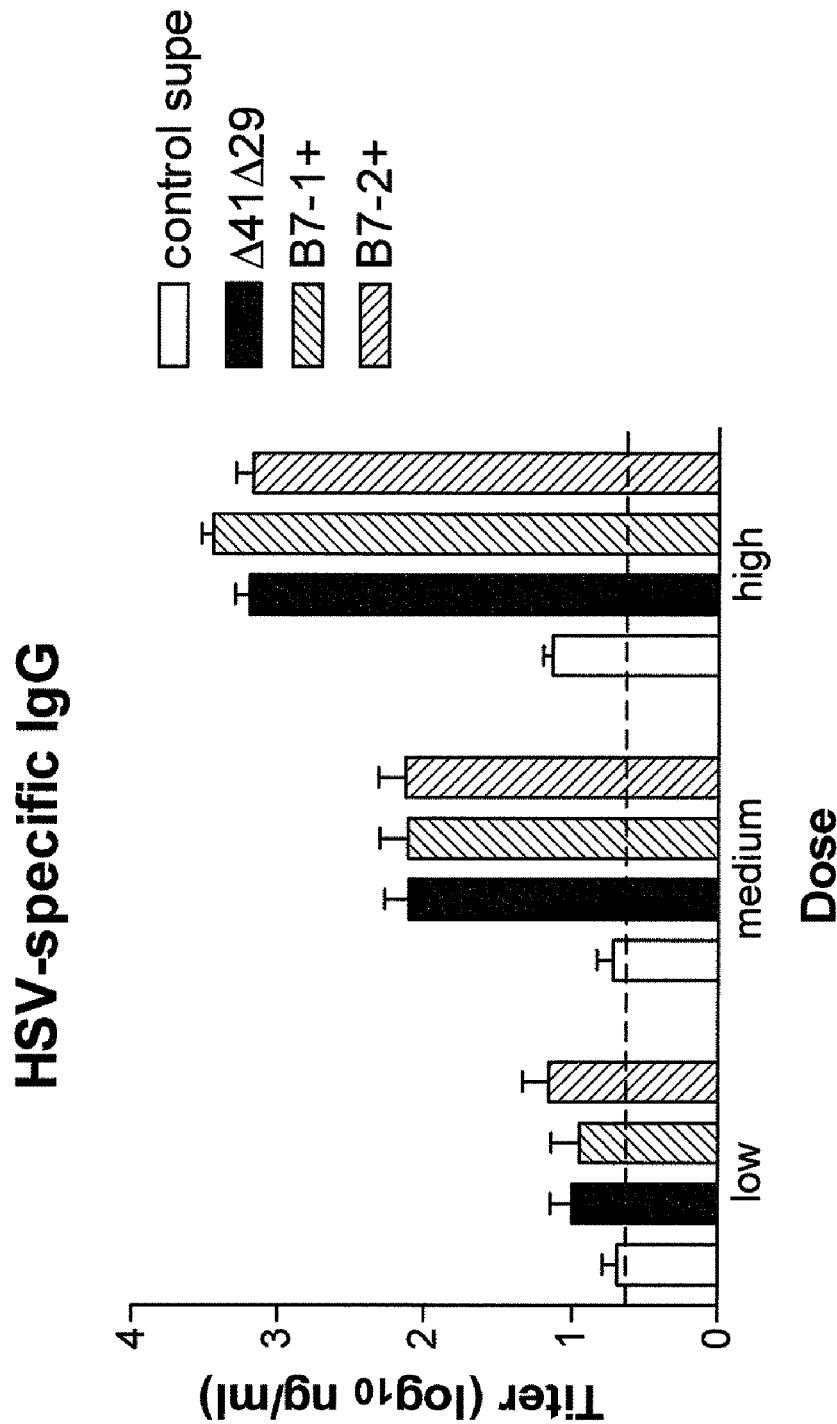
Figure 5:
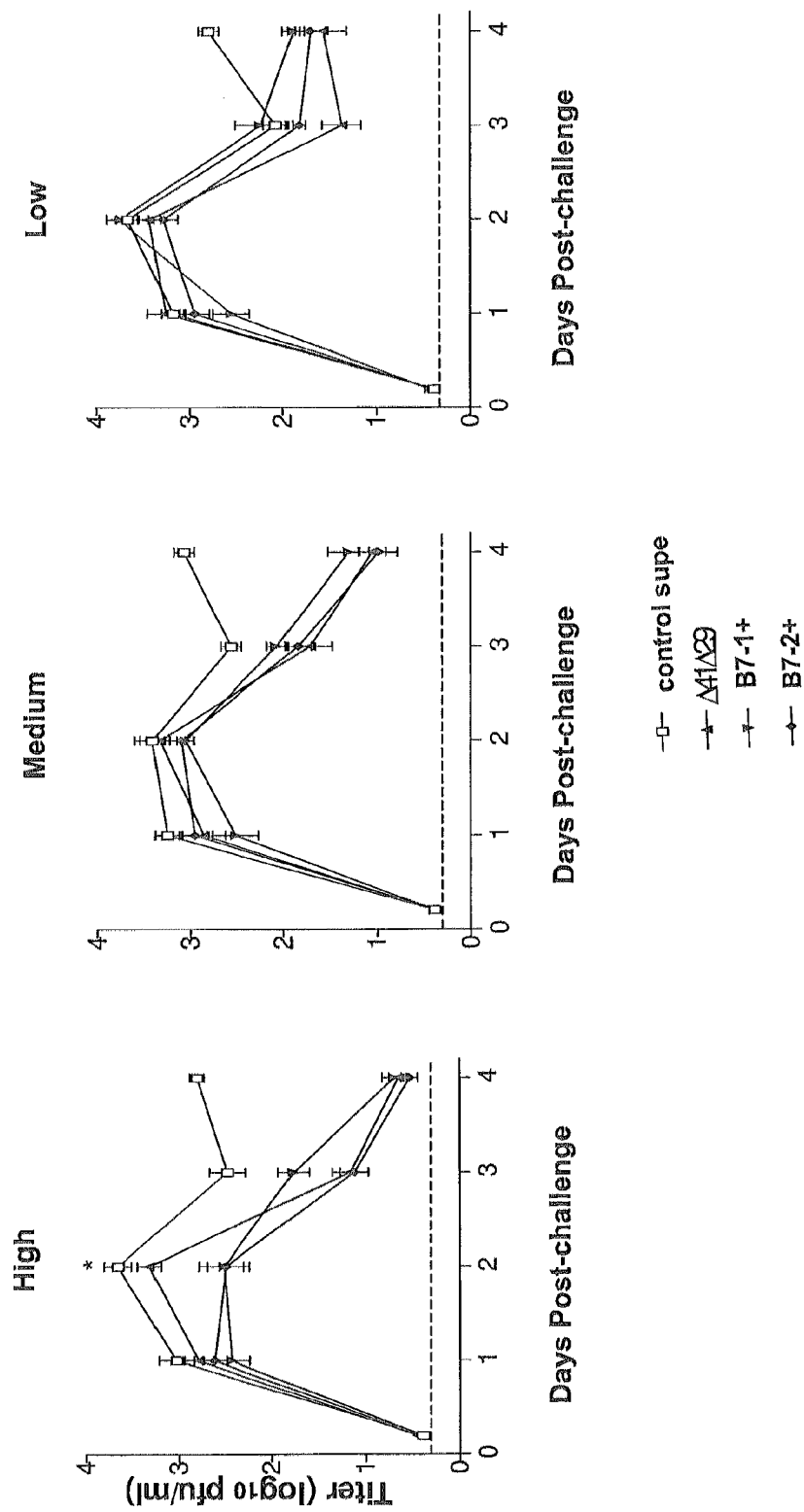
Figure 6:
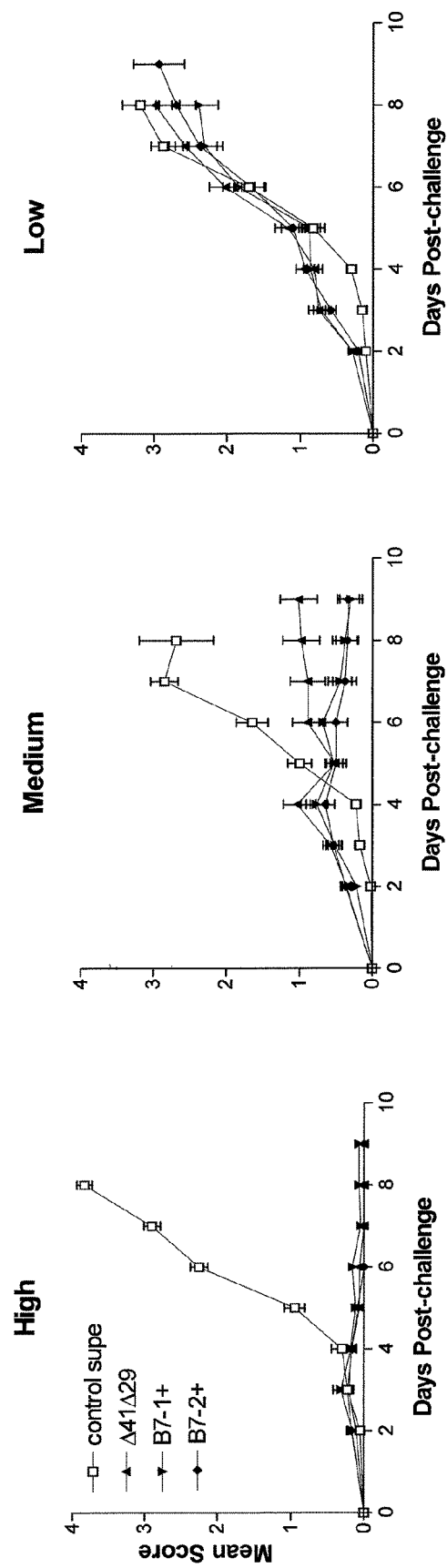
Figure 7:
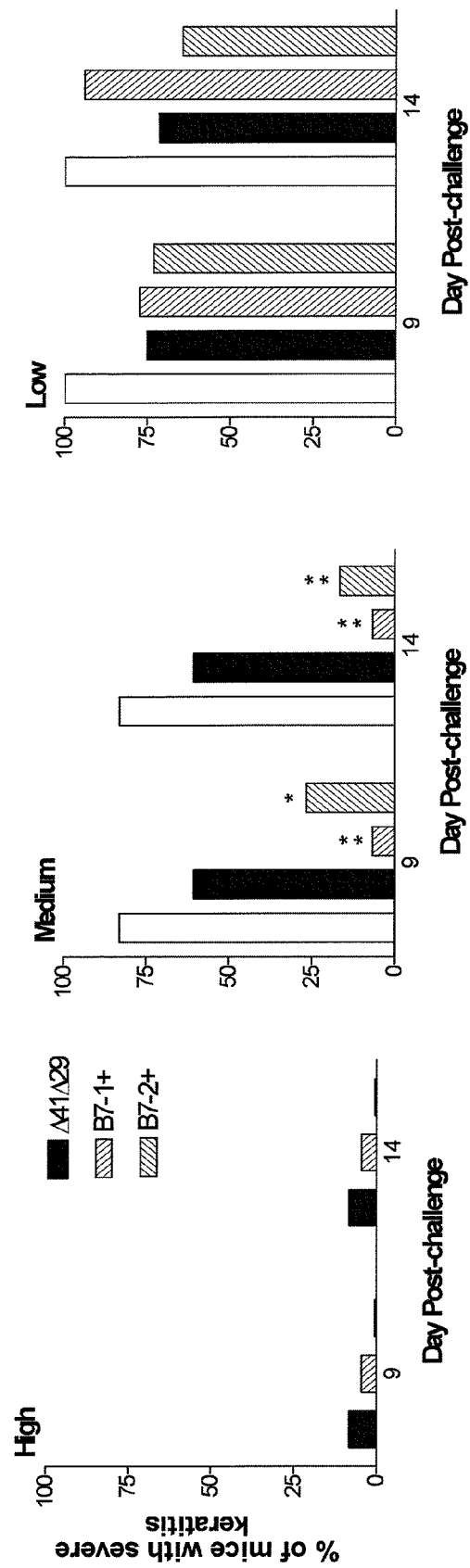
Figure 8:
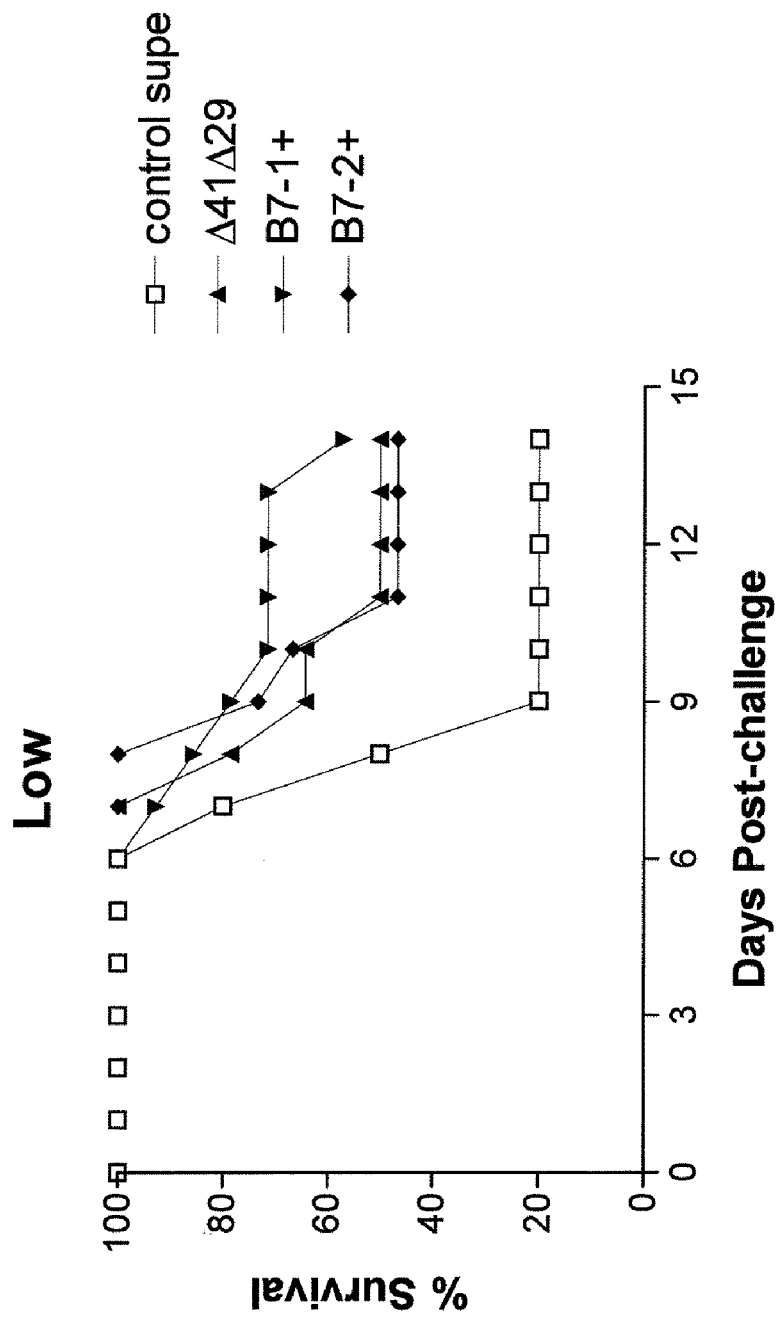
Figure 9:
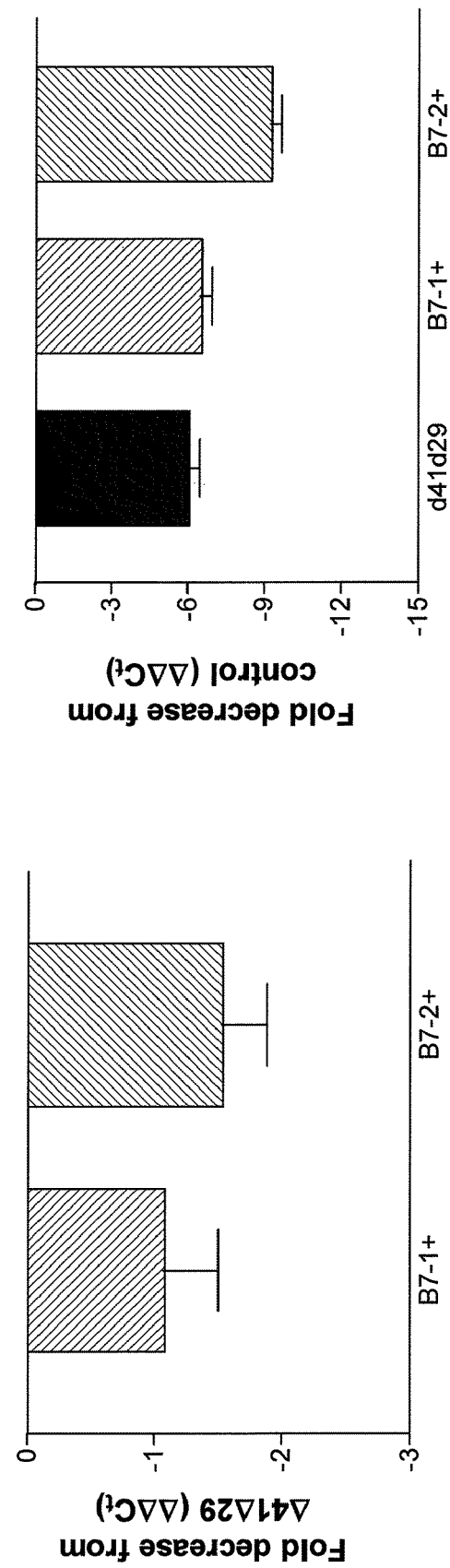

This application is a nonprovisional of and claims the benefit of U.S. Provisional Application Ser. No. 61/078,196, filed Jul. 3, 2008, which document is hereby incorporated by reference to the extent permitted by law.

BACKGROUND OF THE INVENTION

Herpes simplex virus 1 (HSV-1) infections are ubiquitous in the population world-wide, and 65% of the United States population is infected before age 50. Herpes simplex virus 1 (HSV-1) remains a prevalent cause of eye infections, afflicting 450,000 persons in the United States. HSV-mediated ocular diseases include blepharitis, conjunctivitis, and stromal keratitis. Periodic reactivations in infected persons can cause recurrent disease of the cornea. For some, the reactivations lead to corneal scaring and loss of vision; herpetic stromal keratitis is the second most common cause of non-traumatic corneal blindness. Development of an effective vaccine against HSV-1 would help control or prevent this sight-threatening disease.

Moreover, herpes simplex virus types 1 and 2 perpetrate most genital ulcerative disease. Approximately 17% of individuals in the United States are infected with HSV-2, and up to 75% world-wide. HSV-2 infects primarily the genital epithelium where foci of replication cause vesicles to form and ulcerate. The virus also rapidly ascends sensory nerve fibers terminating in the mucosa and enters a latent state in the sensory nerve ganglia, from which it periodically reactivates and travels intra-axonally back to the mucosal epithelium to cause asymptomatic shedding or recurrent disease. Frequency and severity of recurrences reflects the extent of primary and latent infection.

HSV-2 infections typically are sexually transmitted, but also may be transmitted to babies born to HSV-infected women who undergo peripartum primary infection or reactivation. In newborns, the infection often widely disseminates, causing sometimes fatal disease and leaving survivors with long-term sequelae. Vaccines to prevent or treat HSV-2 infections have been sought for decades to alleviate the disease burden. One adjuvanted gD2 glycoprotein preparation has shown some promise, but its efficacy is limited to HSV-seronegative women. Methods to improve current vaccines under development, or new approaches that combine safety with superior efficacy are needed.

The T-cell response to HSV is thought critical to the effective control of infection. Induction of naïve T-cell responses requires three signals: T-cell receptor engagement of the appropriate antigen/MHC molecule, interaction of CD28 with B7-1 and B7-2 costimulation molecules, and cytokines that drive differentiation. Antiviral vaccines, like viruses, must also elicit or provide these same signals in order to induce strong T-cell responses. Some types of vaccine-containing viral glycoprotein or peptide epitopes provide only signal one and are often mixed with adjuvant in order to provide the "danger signals" necessary to elicit signals two and three. DNA vaccines provide signal one to T-cells, but amplify the signal through gene expression in vivo and synthesis of antigen in a form that particularly stimulates CD8 T-cells. Vaccine prototypes consisting of HSV glycoproteins or immunodominant peptide epitopes in adjuvant or plasmid-encoding HSV-1 gD can decrease corneal shedding of HSV-1 and reduce herpes stromal keratitis. Vaccine preparations consisting of or encoding multiple glycoproteins are more potent than a single glycoprotein indicating the benefits of a multivalent vaccine.

Attenuated by replication-competent viruses as vaccines naturally provoke T-cell responses by virtue of their similarity to infection with wild-type virus strains. They also encode numerous external and internal viral proteins that act as targets for immune recognition. Neuroattenuated and single cycle gH mutants of HSV-1 have been explored as potential vaccines for prevented eye disease with success in reducing viral replication and HSV-mediated corneal disease. These forms of replication-competent vaccine may further augment and guide the immune response by encoding cytokines (signal three). For example, a $LAT^{-}g34.5^{-}$ HSV-1 expressing two copies of IL-12p35 improved T-cell activation and elicited higher neutralizing antibody titers than virus without IL-12. These responses correlated with better efficacy against ocular virus replication and establishment of latency. However, titers of $LAT^{-}g34.5^{-}$ HSV-1 are still amplified 10,000-fold in tissue culture, raising concern about the safety of such replication-competent agents.

In answer to the needs for both safety and immunogenicity in a vaccine, replication-defective viruses have also been explored as a means to prevent HSV-1 infection and HSV-mediated eye disease. HSV-1 strains made replication-defective by disruption of the UL29 gene encoding ICP8, essential for viral DNA replication, have shown promise in a mouse model of corneal infection. A single immunization with $ICP8^{-}$ virus reduces HSV-1 replication in the cornea after challenge. Immunization with replication-defective virus also reduces acute and latent infection of the trigeminal ganglia (TG) and incidence of HSK. Replication-defective HSV-1 induces T-cell proliferation and CD8 T-cell responses. CD8 T-cells may protect against immunopathologic damage to the cornea following HSV infection while CD4 T-cells reduce virus replication in the cornea and latent infection in the TG. This basic replication-defective virus has undergone further modification. The virion host shutoff (vhs) protein encoded by UL41 has known immune evasion properties, and immunization of mice with an $ICP8^{-}$ mutant virus increased protection against replication, disease and latency after corneal challenge. Further manipulation of the viral genome may yield additional benefits to immunogenicity and protective capacity of the replication-defective viruses.

SUMMARY OF THE INVENTION

In one of many illustrative, non-limiting aspects of the present invention, there is provided a novel approach for increasing immune response to antiviral vaccines though recombinant DNA technology. More particularly, certain embodiments of the present invention provide an antiviral vaccine that encodes costimulation molecules for increasing immune response to the particular virus at issue. Other objects and features will be in part apparent and in part pointed out hereinafter.

BRIEF DESCRIPTION OF THE SEVERAL VIEWS OF THE DRAWING

The accompanying drawing forms a part of this specification and is to be read in conjunction therewith:

FIG. 1A is a schematic representation of a Southern blot analysis of the tk locus wherein the genomic position of the tk ORF is shown on line 1, an expanded view of this region (line 2) shows the location of EcoRI restriction enzyme sites, the hatched bar depicts the probe fragment used for Southern blot analysis, and line 3 shows the insertion cassette containing the HCMV IEp fused to either the B7-1 (Δ41Δ29B7-1) or B7-2 (Δ41Δ29B7-2) ORF, each of which contains an EcoRI site near the carboxyl terminus;

FIG. 1B is the Southern blot analysis of the tk locus of FIG. 1A wherein genomic DNAs isolated from the Δ41Δ29 parental and recombinant viruses were digested with EcoRI, subjected to electrophoresis, and transferred to membrane, the blot was hybridized to a 32P-labeled fragment of p101086.7 DNA, and the expected sizes of the EcoRI fragments were 2416 bp for Δ41Δ29 (lane 1), 3242 bp for B7-1 virus (lane 2), and 2923 bp for B7-2 virus (lane 3);

FIG. 2 shows B7 molecule expression on the surface of cells infected in vitro with Δ41Δ29B7-1 or Δ41Δ29B7-2 viruses wherein S2 cell monolayers were mock infected or infected at MOI 5 and collected and stained 24 h later with rabbit anti-HSV-2 followed by goat anti-rabbit-PE, and with the appropriate anti-B7-biotin antibody followed by streptavidin-FITC and the cells were analyzed by flow cytometry as follows: A) Mock-infected cells stained with anti-B7-1 and anti-HSV; B) Δ41Δ29B7-1-infected cells stained with anti-B7-1; C) Δ41Δ29-infected cells stained with anti-HSV; D) Δ41Δ29-infected cells stained with anti-B7-1 and anti-HSV-1; E) Δ41Δ29B7-1-infected cells stained with anti-B7-1 and anti-HSV-1; and F) Δ41Δ29B7-2-infected cells stained with anti-B7-2 and anti-HSV-1;

FIG. 3A is a bar chart representation of HSV-specific CD8 T-cell responses induced by immunization wherein: groups of BALB.B mice were immunized with $4 \times 10^5$ pfu of the indicated replication-defective virus or control supernatant; six days after immunization cells from the pooled draining lymph nodes were isolated; and cells were stimulated in vitro with various concentrations of gB498-505 peptide and analyzed in an IFNγ ELISpot assay; and data are the average of duplicate wells;

FIG. 3B shows the HSV-specific CD8 T-cell responses induced by immunization of FIG. 3A wherein cells were stained with CD8 and the $K^b$gB498-505 tetramer and analyzed by flow cytometry, gates were set on CD8+ cells and then analyzed for tetramer staining, and the percentage of CD8+ T-cells that are tetramer-positive is shown for mice immunized with A) control supe, or B) Δ41Δ29, C) B7-1+ and D) B7-2+ viruses;

FIG. 4 is a bar chart representation of pre-challenge HSV-1-specific serum IgG titers wherein groups of BALB/c mice were immunized with low, medium or high doses of the indicated viruses, blood was collected 21 d after immunization and titer of HSV-specific IgG was determined by ELISA, the data represent the geometric mean+SEM compiled from 2 independent experiments (n=10-12);

FIG. 5 is a graphical representation of the titer of challenge virus shed from the corneal epithelium wherein groups of BALB/c mice were immunized with A) high, B) medium or C) low doses of the indicated virus or control supernatant, all groups were challenged 1 mo after immunization by inoculation of HSV-1 mP onto the corneas and mouse eyes were swabbed at the indicated times post-challenge, titers of virus collected on swabs were determined by standard plaque assay, and the data represent the geometric mean+SEM for 10 to 12 samples compiled from 2 independent experiments. *, P=0.002-0.014;

FIG. 6 is a graphical representation of the severity of blepharitis post-challenge wherein mice were immunized with the A) high dose, B) medium dose, or C) low dose of the indicated virus or control supernatant and challenged as described in FIG. 5, blepharitis was scored daily after challenge in masked fashion, and the data represent the mean+SEM for all mice compiled from 2 independent experiments (n=20 eyes for control, and 24 to 30 eyes for virus-immunized mice);

FIG. 7 is a bar chart representation of the incidence of severe keratitis wherein eyes of mice were scored in masked fashion for signs of keratitis 9 d and 14 d post-challenge and the proportion of eyes with severe (sight-damaging) keratitis is shown for groups originally immunized with the A) high dose, B) medium dose, or C) low dose of the indicated virus or control supernatant (n=20 to 30 eyes day 9, 14 to 30 eyes day 14). **, P=0.0003 to <0.0001; *, P=0.0162;

FIG. 8 is a graphical representation of the survival of immunized mice after challenge with HSV-1 wherein the same mice that were immunized and challenged as FIG. 5 were monitored daily for survival, mice were immunized with the low dose of the indicated virus or control supernatant, and the data represent the percentage surviving out of 10 control or 14 to 15 virus-immunized mice per group from 2 independent experiments;

FIG. 9 is a bar chart representation of the relative levels of HSV-1 DNA in trigeminal ganglia during latency wherein: groups of mice immunized with the medium dose of virus or control supernatant were challenged with $8 \times 10^5$ pfu HSV-1 mP 4 wk later; one month after challenge, trigeminal ganglia were removed and DNA was extracted; relative viral DNA content was assessed by real-time PCR using primers for UL50 after normalization of signal to GAPDH and wherein: A) Data represent the relative mean fold decrease (+SD) of latent genome in 11 TG from Δ41Δ29B7-1- and Δ41Δ29B7-2-immunized mice compared with 11 TG from Δ41Δ29-immunized mice (set to 1), P>0.05 by ANOVA; and B) Data represent the relative mean fold decrease (+SD) of latent genome in 11 TG from each group of immunized mice compared with 2 TG, from a mouse immunized with control supernatant that survived the challenge (set to 1); P<0.001 by ANOVA, P<0.001 for each virus-immunized group compared with the control supernatant group by Dunnett t test; and FIG. 10 is a bar chart representation of acute replication of challenge virus in the nervous system wherein mice were immunized with the medium dose of the indicated virus or with control supernatant and challenged by the corneal route one month later, after 3 days mice were sacrificed and trigeminal ganglia and brainstems were dissected, homogenized, and virus titer in them was determined by standard plaque assay, and the data represent the geometric mean+SEM for 10 trigem and 5 brainstem samples per group, *P=0.0337 for B7-2 compared with Δ41Δ29; (P<0.001 for all 3 vaccine virus trigem samples compared with control supernatant; P=0.0045 for B7-2 brainstem sample compared with control supernatant).

DETAILED DESCRIPTION OF THE INVENTION

The present invention generally relates to a novel approach to augment the immune response of a vertebrate host to a virus using an antiviral vaccine or other therapeutic or prophylactic composition that encodes or expresses costimulation molecules within its genome. The present invention is generally applicable to any type of attenuated and replication-defective viral host and antigens and epitopes thereof, including, but not limited to, caudovirales, herpesvirales, mononegavirales, nidovirales, and picornavirales. Specific but non-limiting examples of such viruses include hepadnaviridae including hepatitis B virus (HBV), flaviviridae including human hepatitis C virus (HCV), yellow fever virus and dengue viruses, retroviridae including human immunodeficiency viruses (HIV) and human T lymphotropic viruses (HTLV1 and HTLV2), herpesviridae including herpes simplex viruses (HSV-1 and HSV-2), epstein barr virus (EBV), cytomegalovirus, varicella-zoster virus (VZV), human herpes virus 6 (HHV-6), human herpes virus 8 (HHV-8), herpes B virus, papovaviridae including human papilloma viruses, rhabdoviridae including rabies virus, paramyxoviridae including respiratory syncytial virus, reovitidae including rotaviruses; bunyaviridae including hantaviruses, filoviridae including ebola virus, adenoviriidae, parvoviridae including parvovirus B-19, arenaviridae including lassa virus, orthomyxoviridae including influenza viruses, poxviridae including orf virus, molluscum contageosum virus and monkey pox virus, togaviridae, coronaviridae including corona viruses, and picornaviridae. For the purposes of illustration only, the present invention will be described in connection with herpes simplex virus 1 (HSV-1) or herpes simplex virus 2 (HSV-2) in mice, but one skilled in the art will appreciate that the methods and compositions described herein may be applied to any virus and vertebrate suitable for use in the present invention.

A viable vaccine candidate must meet goals of both safety and efficacy. While attenuated vaccines may be used in the present invention, replication-defective vaccines are often considered to be the safest form of live virus vaccine because they do not reproduce and spread in the recipient. Replication-defective vaccines also express numerous viral proteins in infected cells that stimulate broad spectrum antiviral immunity and further manipulation of prototype replication-defective virus vaccines may enhance their immunogenicity and effectiveness. Moreover, an optimal immune response to an anti-viral vaccine requires viral antigens to be presented in a context in which ample costimulation occurs. For the purposes of illustration only, the following disclosure is presented using B7 costimulatory molecules; however, it will be appreciated by one skilled in the art that any suitable costimulation molecule may be used in the present invention.

In mice lacking both B7-1 and B7-2 (B7KO), the increased severity of HSV infection has confirmed the importance of these molecules in generation of HSV-specific immunity. To test the concept that B7-1 or B7-2 expression by replication-defective HSV could augment its immunogenicity and protective capacity, the present inventors constructed replication-defective HSV-2 encoding B7-1 or B7-2. Both viruses partially reconstituted immune responses to HSV compared with replication-defective virus alone when used to immunize B7KO mice, indicating that the increased responsiveness to virus could be attributed to virus-encoded B7 molecules. Furthermore, replication-defective HSV-2 encoding B7-2 conferred better protections against HSV-2 infection to wild-type mice than did the parent replication-defective virus even though wild-type mice express endogenous B7 molecules. To determine whether provision of additional "signal two" could improve the immunogenicity and capacity of ICP8$^-$vhs$^-$ HSV-1 to protect against HSK, the present inventors constructed and tested ICP8$^-$vhs$^-$ viruses that encode B7 costimulation molecules within their genome.

B7 costimulation molecules, encoded by the replication-defective, vhs-virus help the vaccine strain achieve greater protection of mice from stromal keratitis induced by HSV-1 challenge than vhs-, replication-defective virus lacking B7. Virus-encoded B7-1 and B7-2 equally improved vaccine-mediated protection from keratitis, and this protection could be observed using a dose of only $4\times10^4$ pfu of cell-free replication-defective virus. The increased efficacy of B7-expressing viruses correlated with enhanced, virus-specific CD4 and CD8 T-cell responses. B7-2-expressing virus also protected the CNS from acute infection significantly better than virus lacking B7. Both B7-1 and B7-2-expressing viruses showed a distinct, though not statistically significant, trend toward improving blepharitis, latent viral genome load and survival. Thus, provision of signal two for T-cells by the HSV-1 vaccine strain enhanced protection from keratitis mediated by HSV-1 itself.

In one embodiment of the present invention, deletion of from a replication-defective vaccine strain of HSV-1 amplified immune responses and enhanced its capacity to protect against corneal infection with virulent HSV-1. The method of the present invention including the expression of expressing host costimulation molecules from the genome of a replication-defective HSV-1 vaccine achieved even greater protection against HSV-1-induced keratitis, in some manner by providing signal two on the virus-infected cell to responding T-cells.

B7-1 and B7-2 costimulation enhances numerous aspects of the antiviral immune response, including enhancement of cytokine production, proliferation, cytotoxicity, and antibody production. Conversely, when B7-2 is blocked by specific antibody treatment, CD8 T-cell cytotoxic activity declines and HSV-1 corneal infection worsens. The critical signals mediated by B7-1 and B7-2 operate at different temporal phases of T-cell activation. B7-2 is constitutively expressed and rapidly upregulated, whereas B7-1 expression on professional APC must be provoked. Thus, the present inventors anticipated that B7-2 might stimulate stronger immunity and achieve better protective efficacy than the virus encoding B7-1. However, B7-1 and B7-2-expressing viruses generated similar levels of protection from HSV-1 corneal infection and this was reflected in equivalent levels of virus-specific antibody and T-cell responses.

Precedent exists for the beneficial activity of virus-encoded B7 costimulation molecules as a strategic element of vaccines. B7-1 and B7-2 encoded by vaccinia or adenovirus vectors markedly augment immunogenicity of coexpressed tumor antigens, and help reduce tumor burden in animal models. Our viruses encoding B7 costimulation molecules represent a new direction in that they enhance the immune response to the pathogen itself. Noninfectious HSV particles engineered to contain B7 costimulation molecules on their surface also induce stronger immune responses than particles without, supporting the idea of providing B7 costimulation molecules in conjunction with virus antigens to artificially create an antigen presenting cell. ICP8$^-$ HSV-2 expressing B7-2 and ICP8$^-$ HSV-1 additionally lacking vhs are each highly immunogenic. Indeed, a great deal of protection could be achieved with a single, low immunizing dose. With ICP8$^-$vhs$^-$B7$^+$ HSV-1, the present inventors established a lower limit of immune effector activity in BALB/c mice with the dose of $4\times10^3$ pfu. This dose generated immune responses that still reduced replication in the corneal epithelium by 4 days post-infection and improved the survival rate, but did not significantly impact the incidence or severity of blepharitis or keratitis. By increasing the dose to just $1\times10^4$ pfu, significant protection against HSK was also achieved. Therefore, as used herein, administration of an "effective amount" of the virus-expressing host costimulation molecules hereof is defined as an amount effective, at dosages and for periods of time necessary to achieve the desired result. The effective amount of the virus-expressing host costimulation molecules of the invention may vary according to factors such as the disease state, age, sex, and weight of the animal. Dosage regima may be adjusted to provide the optimum therapeutic response. For example, several divided doses may be administered daily or the dose may be proportionally reduced as indicated by the exigencies of the therapeutic situation.

Thus, the present invention includes pharmaceutical compositions containing virus-expressing host costimulation molecules for use in enhancing an immune response. Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions. The pharmaceutical compositions of the invention can be intended for administration to vertebrates. Dosages to be administered depend on individual needs, on the desired effect and on the chosen route of administration. The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other immunostimulatory agents to enhance the immune response.

Example 1

Cells and viruses. The replication-defective mutant of HSV-1 KOS, Δ41Δ29 has defects in expression of vhs and the essential gene product ICP8 due to insertion of a nonsense linker in the UL41 open reading frame (ORF) at amino acid position 238 and disruption of the UL29 ORF by insertion of a lacZ expression cassette, respectively. Δ41Δ29 was propagated in S2 cells, a Vero cell line stably expressing ICP. Δ41Δ29 was further mutated to contain a murine B7-1 (CD80) or B7-2 (CD86) expression cassette. CD80 and CD86 open reading frames cloned downstream of the HCMV immediate early enhancer/promoter in plasmids pBS (HCMV/B7-1) and pEH48(HCMV/B7-2) were excised and inserted into a BglII site previously engineered 751 bp from the 5' end of the thymidine kinase (tk) ORF in plasmid p101086.7BglII. These plasmids were cotransfected with full-length Δ41Δ29 DNA into S2 cells using nucleofection (Amaxa Biosystems) according to the manufacturer's protocol. To select B7-expressing recombinant viruses, S2 cells infected with virus progeny of the cotransfection were incubated in the presence of 100 μM acyclovir. Potential recombinant viruses able to grow in the presence of acyclovir were grouped in pools. Fresh cells infected with each pool were screened by flow cytometry for expression of B7 molecules. Isolates from positive pools were individually re-screened by flow cytometry and then triply plaque-purified. Insertion into tk was confirmed by Southern blot analysis. The B7-1- and B7-2-expressing viruses were named Δ41Δ29B7-1 and Δ41Δ29B7-2, respectively. Viruses used for immunizations were produced free of cell debris by isolation from the supernatant of infected cell monolayers using high speed centrifugation. HSV-1 strain microplaque (mP) was propagated in Vero cells. Virus titers were determined on S2 or Vero cells by standard plaque assay.

Mice. Female BALB/c mice were purchased from the National Cancer Institute. Female BALB.B mice (H-$2^b$) were purchased from The Jackson Laboratories. All mice were housed at Saint Louis University under specific-pathogen-free conditions in accordance with institutional and federal guidelines, and were used at 6 weeks of age.

Flow cytofluorometric analyses. S2 cells infected with potential recombinant plaque isolates were stained 24 hr late by addition of anti-B7-1 or B7-2-biotin (1:150; PharMingen/Becton-Dickinson), followed by streptavidin-FITC (1:150; Immunotech) and analyzed by flow cytometry on a FACS-Calibur. For demonstration of B7 expression by Δ41Δ29B7-1 and Δ41Δ29B7-2, S2 cells were stained 24 hr after infection at MOI of 5 by addition of anti-B7-1 or B7-2 biotin and anti-HSV-1 rabbit antiserum (1:100; Dako), followed by streptavidin-FITC and goat anti-rabbit-PE (1:100; Vector Laboratories) secondary reagents, respectively.

Southern blot hybridization. Viral DNAs were purified from potential recombinant viruses using a Qiagen QIAamp DNA Mini Kit according to the manufacturer's instructions. One μg of each DNA sample was subjected to EcoRI restriction digestion, and fragments were separated on a 0.8% agarose gel. DNA fragments were transferred to Hybond-N+ nylon membrane (Amersham) by capillary diffusion and hybridized to a randomly primed, [$^{32}$P]-labeled SacI fragment of plasmid p101086.7 used as a probe. Images were obtained on X-ray film by autoradiography.

Immunization of mice. For immunization, hind flanks of mice were injected subcutaneously (s.c.) with $4\times10^5$ pfu (high), $4\times10^4$ pfu (medium), or $4\times10^3$ pfu (low) doses of virus suspended in 40 μl total vol of normal saline. Cohorts of mice received an equivalent amount of supernatant concentrated from uninfected cell cultures as a negative control for immunization.

Assays of T-cell response. CD8 T-cell responses induced by vaccination were compared by ELISpot assays and tetramer staining of BALB.B mice immunized as described above. For ELISpot assays, groups of BALB.B mice were immunized with $4\times10^5$ pfu (acute ELISpot and tetramer) or $4\times10^4$ pfu (recall tetramer) of the various vaccine strains or an equivalent amount of control supernatant s.c. in the hind flank. Draining lymph nodes were removed 6 d later and $3\times10^6$ cells were added per well in duplicate to Milliscreen-HA plates (Millipore) previously coated with antibody to IFNγ (BD Pharmingen). HSV-1 gB peptide 498-505 was added to the cultures at the indicated concentrations. After incubation for 20 hr, plates were washed extensively to remove cells and IFNγ captured on the membrane was detected using a biotinylated anti-IFNγ antibody (BD Pharmingen), followed by streptavidin conjugated to alkaline phosphatase (BDPharmingen) and BCIP-NBT (Sigma). Spots were counted using an Immunospot plate reader (v. 5.0; Cellular Technology, Ltd.).

For tetramer staining, $10^6$ cells per sample were incubated in FcBlock (BD Biosciences) and stained with phycoerythrin-labeled $K^b$-gB498-505 tetramers at 1:100 for 20 min at 37° C. Cells were then washed, fixed and stained with FITC-labeled anti-CD8 clone CT-CD8a at 1:30 dilution on ice. Cells were observed by flow cytometry using an LSRII (Becton Dickinson) and analyzed using FloJo 8.0 software.

Quantitation of serum antibodies. To determine the titer of HSV-specific serum antibodies induced by vaccination, mice were unimmunized or immunized with 5BlacZ, 5B86 or control supernatant. Blood was collected from the tail vein of mice 21 days after immunization. Serum was prepared by clot retraction and analyzed by ELISA. Anti-mouse-IgG-biotin (R & D Systems, Minneapolis, Minn.) was used as secondary antibody and detected using streptavidin-HRP followed by OPD substrate (Sigma, St. Louis, Mo.). Plates were read at 490 nm on a BioRad 680 reader. Antibody titers were determined by comparison to standard curves generated with serum containing known concentrations of IgG captured on plates coated with goat-anti-kappa light chain antibody (Caltag).

In vivo challenge. Four wk after immunization, mice were anesthetized by intraperitoneal injection of ketamine/xylazine, and infected with 5 µl HSV-1 mP inoculated onto each scarified cornea for a dose of $8 \times 10^5$ pfu. To measure virus replication in the corneal epithelium, eyes were swabbed with moistened cotton-tipped swabs at 4 hr and days 1 through 5 post-infection. Swabs for each mouse were placed together in 1 ml PBS and stored frozen until assay. Virus was quantified on Vero cell monolayers by standard plaque assay. After challenge, body weight, signs of disease and survival were monitored on a daily basis. Mice were weighed individually and mean change from initial body weight was calculated daily for each group. Blepharitis scores were assigned in a blinded fashion based on the following scale: 0—no apparent signs of disease; 1—mild swelling and erythema of the eyelid; 2—moderate swelling and crusty exudate; 3—periocular lesions, and depilation; and 4—extensive lesions, and depilation. Mean daily disease score was calculated for each group. Keratitis was assessed at 9 d and 14 d post-challenge using an opthalmoscope and the proportion of eyes with dense opacity (3+) or complete opacity with corneal ulceration (4+) was recorded. Virus replication in neural tissue was analyzed by dissection of trigeminal ganglia and brainstems from a cohort of mice 4 d after challenge. Tissues were stored frozen until use. For virus titer determination, the tissues were thawed and disrupted using a Mini-Bead Beater (BioSpec, Inc.), and then diluted for standard plaque assay.

Assessment of latency by real-time PCR. TG were collected from surviving mice 30 d post-infection and stored at −80° C. DNA was isolated from the TG using a QIAamp DNA Mini Kit (Qiagen) according to the manufacturer's instructions. PCR reactions were run in 25 µl reaction vol using FastStart SYBR Green Master (Rox) (Roche), and primers at 300 nM final concentration. For GAPDH, reactions used 10 ng template DNA and primers forward 5'-GAGTCTACTGGCGTCTTCACC-3' and reverse 5'-ACCATGAGCCCTTCCACAATGC-3' which amplify a 337 bp product. For HSV-1 UL50, reactions used 125 ng template DNA and primers forward 5'-CGGGCACGTATGT-GCGTTTGTTGTTTAC-3' and reverse 5'-TTCCTGGGT-TCGGCGGTTGAGTC-3' which amplify a 195 bp product. Reactions were performed using an ABI Prism 7500 real-time PCR system (Applied Biosystems) and cycle conditions: 2 min at 50° C., 10 min at 95° C., 40 cycles of 95° C. for 15 sec and 60° C., and dissociation at 95° C. for 15 sec. Specificity was verified by melting curve analysis. The average of duplicate wells yielded the Ct value, and the UL50 signal for each sample was normalized to the GAPDH signal content by determination of ΔCt. Fold decrease in UL50 content of TG from Δ41Δ29B7-1 and Δ41Δ29B7-2 immunized mice relative to mice receiving Δ41Δ29 was determined using the $2^{(\Delta\Delta Ct)}$ method (Livak K J and Schmittgen; Pfaffl M W 2001). Fold decrease in UL50 content of TG from immunized mice relative to TG from a mouse receiving control supernatant was determined using the $2^{(\Delta\Delta Ct)}$ method (Livak K J and Schmittgen; Pfaffl M W 2001). To ensure accuracy of the UL50 level in the two TG from the control supernatant group, the TG were thrice assayed in duplicate and the average ΔCt was calculated from the 6 values obtained.

Statistics. Significance of difference in virus or antibody titers on individual days was determined by Student's t test. Proportion of mice with keratitis or surviving infection was compared using the Fisher exact method. The Kruskal-Wallis non-parametric test was used to assess the significance of difference in blepharitis scores on individual days post-challenge. Relative levels of latent viral DNA between immunization groups were compared by one way analysis of variance (ANOVA) with the Bonferroni post hoc test for multiple groups. Each virus-immunized group was compared with the control supernatant group using the Dunnett t post hoc test. Only one mouse immunized with control supernatant survived challenge; however, a test of homogeneity of variances was not significant.

Results.

In vitro characterization. The murine B7-1 and B7-2 ORFs downstream of the HCMV IEp were inserted into the HSV-1 thymidine kinase (tk) (UL23) ORF in plasmid p101086.7BglII at a unique BglII site engineered 751 bp from the 5' end of the ORF. The resulting plasmids were cotransfected into S2 cells with full-length DNA from the replication-defective HSV-1 strain Δ41Δ29 which contains a lacZ insertion in the ICP8 ORF and a deletion in the vhs ORF as shown in FIG. 1A. Plaques were isolated from the cotransfection mixture in the presence of acyclovir, and cells infected with the plaque isolates were screened for expression of B7 molecules by flow cytometry and triply plaque-purified. B7-1- and B7-2-expressing recombinants were named Δ41Δ29B7-1 and Δ41Δ29B7-2, respectively. Southern blot analysis was used to verify insertions into the tk ORF in Δ41Δ29B7-1 and Δ41Δ29B7-2 as shown in FIG. 1B. Genomic DNAs purified from the Δ41Δ29 parental and potential recombinant viruses were restricted with EcoRI, electrophoresed, transferred to membrane, and hybridized to a $^{32}$P-labeled fragment of p101086.7 DNA. The Southern blot of Δ41Δ29 showed a single fragment of expected size (2.4 kb as shown in FIG. 1B, lane 1), and single fragments of expected sizes, 3.2 kb and 2.9 kb for the B7-1- and B7-2-containing viruses, respectively, as shown in lanes 2 and 3 of FIG. 1B.

Expression of B7 costimulation molecules on the surface of cells infected in vitro with Δ41Δ29B7-1 or Δ41Δ29B7-2 was verified by flow cytometry. S2 cells were mock infected or infected at MOI 5 and collected and stained 24 h later with anti-B7-1 and B7-2 antibodies. Mock-infected cells showed no staining above background, whereas cells infected with Δ41Δ29B7-1 or Δ41Δ29B7-2 stained brightly with B7-1 or B7-2, respectively, as shown in FIGS. 2B and C. Thus, host costimulation molecules expressed from the HSV genome are expressed at uniformly high levels on the infected cell surface.

Immune response to immunization. The capacity of B7 costimulation molecules expressed from the immunizing virus to elicit cellular and humoral immune responses was determined. CD8 T-cells were analyzed because they are thought to play a dominant role in suppressing virus replication in the cornea and trigeminal ganglia. To determine the capacity of the various vaccine prototype strains to elicit HSV-specific CD8 T-cells, mice were immunized s.c. with $4 \times 10^4$ pfu of the parental replication-defective/vhs⁻ virus Δ41Δ29, Δ41Δ29B7-1 or Δ41Δ29B7-2, or an equivalent amount of control supernatant. Six days later cells in the draining lymph nodes were analyzed by IFNγ ELISpot specific for CD8 T-cells recognizing the immunodominant epitope gB498-505 restricted by H-2K$^b$. Mice immunized with control supernatant showed very low background of IFNγ-producing cells (FIG. 3A). Δ41Δ29, Δ41Δ29B7-1 and Δ41Δ29B7-2 all stimulated strong HSV-specific responses from CD8 T-cells in the draining lymph nodes acutely after immunization, with a slightly greater response from mice immunized with Δ41Δ29B7-2 (FIG. 3B). This observation was corroborated by analysis using tetramer staining of CD8 T-cells specific for the gB498-505 epitope. Some binding of tetramer to CD8+ cells from mice immunized with control supernatant was routinely observed (FIG. 3B and Table 1).

TABLE 1

CD8+, tetramer+ cells in the draining lymph nodes 6 d after immunization.

| Immunization | Cells recovered | % CD8+ tetramer+ cells | Total CD8+ tetramer+ cells |
|---|---|---|---|
| Control supe | $1.0 \times 10^7$ | 0.8 | $1.3 \times 10^4$ |
| ☐41☐29 | $1.2 \times 10^7$ | 2.1 | $4.2 \times 10^4$ |
| B7-1+ | $1.3 \times 10^7$ | 2.9 | $5.3 \times 10^4$ |
| B7-2+ | $1.9 \times 10^7$ | 2.6 | $8.3 \times 10^4$ |

However, staining of cells from mice immunized with Δ41Δ29 was greatly increased over staining of cells from mice receiving control supernatant (FIG. 3B and Table 1). Mice immunized with Δ41Δ29B7-1 or Δ41Δ29B7-2 both contained a slightly higher percentage and absolute number of tetramer+ CD8+ cells in the draining lymph nodes 6 days after immunization than mice immunized with Δ41Δ29 (Table 1). Collectively, these assays suggest slightly stronger stimulation of acute HSV-specific T-cell responses by replication-defective viruses when the viruses express B7-1 or B7-2 costimulation molecules.

A tetramer assay was also performed on cells in the draining lymph nodes of mice 6 d after corneal challenge. Cervical lymph node cells from mice immunized with either B7-1 or B7-2-expressing viruses stained more heavily with the gB498-505 tetramer than cells from ☐41☐29- or control supernatant-immunized mice, and yielded twice as many tetramer-positive cells (Table 2). Thus, vaccinated mice responding to HSV-1 ocular challenge have more HSV-specific T-cells available to fight the infection if exogenous B7-1 or B7-2 was expressed by the immunizing virus.

TABLE 2

CD8+, tetramer+ cells in the draining lymph nodes 6 d after corneal challenge.

| Immunization[a] | Cells recovered | % CD8+ tetramer+ cells | Total CD8+ tetramer+ cells |
|---|---|---|---|
| Control supe | $1.9 \times 10^8$ | 1.9 | $3.8 \times 10^6$ |
| ☐41☐29 | $1.0 \times 10^8$ | 2.5 | $2.5 \times 10^6$ |
| B7-1+ | $1.8 \times 10^8$ | 3.2 | $5.9 \times 10^6$ |
| B7-2+ | $1.2 \times 10^8$ | 4.6 | $5.3 \times 10^6$ |

[a]Mice were immunized with $4 \times 10^4$ pfu of the indicated virus and challenged 28 d later.

The capacity of the vaccines to elicit HSV-specific antibody was determined by immunizing groups of mice s.c. with $4 \times 10^5$ pfu (high), $4 \times 10^4$ pfu or $4 \times 10^3$ pfu (low) doses of the parental ICP8−/vhs− virus Δ41Δ29B7-1 or Δ41Δ29B7-2. Three weeks after immunization, blood was collected and HSV-specific IgG titers in the serum were determined by ELISA. Antibody titers elicited by Δ41Δ29B7-1 or Δ41Δ29B7-2 were not significantly greater than that induced by Δ41Δ29 at all three immunizing doses (FIG. 4). Thus, Δ41 Δ29B7-1 and Δ41Δ29B7-2 induced somewhat stronger HSV-specific T-cell responses by this did not manifest as additional help for antibody production.

Protective effect of the vaccines. At 4 wk post-challenge, mice were challenged on the cornea with the virulent HSV-1 strain mP. Replication in the corneal epithelium was quantified over the first 4 days post-challenge by titer of virus collected on corneal swabs. Mice immunized with control supernatant sustained high levels of challenge virus replication in the corneal epithelium (FIG. 5). The Δ41Δ29 parental virus had no effect on challenge virus replication at day 1 or day 2 post-challenge at any immunizing dose. In contrast, by day 2, immunization with the high dose of B7-1 or B7-2-expressing viruses was able to reduce challenge virus replication 200-fold compared to control-immunized mice, and 50-fold compared Δ41Δ29 (FIG. 5A). Immunization of mice with the high dose of all three replication-defective viruses helped mice nearly resolve HSV-1 replication in the cornea by day 4 post-challenge (FIG. 5A). At the medium immunizing dose, the three replication-defective viruses significantly reduced challenge virus replication by 3 days post-challenge and even more so by 4 days post-challenge (FIG. 5B). However, neither B7-expressing virus improved protection over what was observed with Δ41Δ29. At the lowest immunizing dose, all replication-defective viruses equivalently reduced challenge virus replication in the corneal epithelium, but only at 4 days post-challenge (FIG. 5C). Thus, addition of B7-1 or B7-2 to an ICP8−vhs− vaccine strain has a transient but significant impact on protection of the corneal epithelium when given at the high ($4 \times 10^5$ pfu) immunizing dose.

Blepharitis developed in mice immunized with control supernatant by 4 days post-challenge, and became severe by 7 d post-challenge (FIG. 6). In marked contrast, all 3 replication-defective vaccine strains protected mice almost completely from developing any inflammation of the eyelid (FIG. 6A). When given at the medium dose, Δ41Δ29 protected mice from severe blepharitis, but moderate inflammation was observed from 4 through at least 9 days post-challenge (FIG. 6B). In contrast, in mice immunized with Δ41Δ29B7-1 and Δ41Δ29B7-2, blepharitis was mild and decreased from 4 through 9 d post-challenge (FIG. 6B), though the difference with Δ41Δ29 did not achieve statistical significance. The lowest immunizing dose did not afford protection from blepharitis to any of the mice (FIG. 6C), although fewer eyelids of those immunized with any of the viruses showed periocular lesions. Thus, vaccine strains encoding either B7-1 or B7-2-slightly enhanced protection from blepharitis over that afforded by Δ41Δ29 after HSV-1 ocular infection.

Keratitis was assessed in all surviving mice at 9 and 14 d post-challenge. Δ41Δ29 given at the high dose protected mice almost completely from developing severe (sight-impairing) keratitis, and no mouse immunized with the high dose of Δ41Δ29B7-2 showed severe corneal disease (FIG. 7A). At the medium immunizing dose, 80% of mice receiving control supe had sight-compromising corneal disease (FIG. 7B). Mice immunized with Δ41Δ29 showed slightly less disease incidence, but 60% of corneas still were severely affected. In contrast, prior immunization of mice with the medium dose of either B7-1 or B7-2-expressing virus very significantly protected them from developing severe corneal disease after HSV-1 infection (FIG. 7B). When given at the low dose, all three vaccine strains only slightly reduced the incidence of severe keratitis compared with control supernatant (FIG. 7C). Thus, immunizations using the medium dose ($4 \times 10^4$ pfu) revealed a significant capacity of B7 molecules, encoded by the vaccine virus, to enhance protection from development of keratitis afforded by replication-defective/vhs-virus.

The HSV-1 mP strain causes a virulent infection when inoculated by the corneal route. Ocular challenge with mP resulted in the death of most mice immunized with control supernatant by 9 d post-challenge (FIG. 8). Prior immunization with the ICP8−/vhs− parental virus or either strain encoding B7 molecules completely protected mice from lethal infection when given at the high or medium doses (data not shown). Even when as few as 4000 pfu of supernatant-derived vaccine virus (low dose) was used, at least half of the mice were subsequently protected from lethal infection (FIG. 8). The B7-1-expressing virus prolonged survival compared with parental or B7-2-expressing vaccine strains, but ultimately no significant difference between the three vaccine strains in capacity to protect against mortality was observed.

We also determined whether the B7-1 or B7-2 vaccine viruses enhanced protection of the nervous system compared with the ICP8⁻vhs⁻ parental virus. Mice immunized with medium dose of vaccine were chosen for analysis because this dose had permitted the best distinction between immunizing strains based on parameters of disease. To assess vaccine capacity to reduce establishment of latent infection, TG were removed from mice 1 month after challenge and their burden of latent challenge virus genome was assessed. DNA was prepared from individual TG and subjected to real-time PCR using primers for UL50 to detect viral genomes and for GAPDH as a normalization control (FIG. 9). B7-1 and B7-2 afforded slightly better protection from latent infection of the nervous system by challenge virus than Δ41Δ29 (FIG. 9A), although the difference was not statistically significant. All three vaccine strains reduced latent infection of the TG by challenge virus to 8-fold when compared with the genome load in TG of a mouse immunized with control supernatant that survived challenge (FIG. 9B). This result may underestimate the difference between virus-immunized and control animals because the vast majority of mice immunized with control supernatant are so extensively infected that they do not survive challenge.

To determine whether protection from keratitis by Δ41Δ29B7-1 and Δ41Δ29B7-2 viruses was related to the level of challenge virus reaching the nervous system acutely after challenge, TG and brainstems were isolated from immunized mice sacrificed 3 d post-challenge and virus titer in the tissues was determined All vaccine strains protected the nervous system better than control supernatant (FIG. 10). B7-1 and B7-2 showed a trend toward better protection against acute infection of the nervous system by the challenge virus than Δ41Δ29, although only B7-2 improved protection to a statistically significant degree.

Having described the invention in detail, those skilled in the art will appreciate that modifications may be made of the invention without departing from the spirit and scope thereof. Therefore, it is not intended that the scope of the invention be limited to the specific embodiments described. Rather, it is intended that the appended claims and their equivalents determine the scope of the invention.

We claim:

1. A pharmaceutical composition for use in enhancing an immune response to herpes simplex virus (HSV) comprising an effective amount of a B7 costimulation molecule-expressing, replication-defective ICP8⁻ HSV and a carrier, wherein after administration of said pharmaceutical composition to a vertebrate, said costimulation molecule is expressed on the surface of infected cells.

2. The pharmaceutical composition of claim 1, wherein said HSV is virion host shutoff protein deficient.

3. The pharmaceutical composition of claim 1, wherein said HSV is a ICP8⁻vhs⁻B7⁺ HSV-1 or -2 replication-defective virus.

4. A method of enhancing an immune response to herpes simplex virus (HSV) in a vertebrate comprising the steps of: administering an effective amount of a B7 costimulation molecule-expressing replication-defective HSV and a carrier prior to HSV infection, wherein after administration of said pharmaceutical composition to said vertebrate, said costimulation molecule is expressed on the surface of infected cells.

5. The method of claim 4, wherein said HSV is an ICP8⁻ defective virus.

6. The method of claim 4, wherein said HSV is virion host shutoff protein deficient.

7. The method of claim 4, wherein said HSV is a ICP8⁻vhs⁻B7⁺ HSV-1 or -2 replication-defective virus.

8. A method of manufacturing a pharmaceutical composition for enhancing an immune response to herpes simplex virus comprising the steps of: combining an effective amount of a B7 costimulation molecule-expressing ICP8⁻ replication-defective herpes simplex virus and a carrier, wherein said virus expresses said costimulation molecule on the surface of infected cells after administration of said pharmaceutical composition to a vertebrate.

9. The method of claim 8, wherein said HSV is virion host shutoff protein deficient.

10. The method of claim 8, wherein said virus is an ICP8⁻vhs⁻B7+ HSV-1 or -2 replication-defective virus.

* * * * *

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: PCR Forward Primer

<400> SEQUENCE: 1
gagtctactg gcgtcttcac c                                         21

<210> SEQ ID NO 2
<211> LENGTH: 22
<212> TYPE: DNA
<213> ORGANISM: Artificial Sequence
<220> FEATURE:
<223> OTHER INFORMATION: PCR Reverse Primer

<400> SEQUENCE: 2
accatgagcc cttccacaat gc                                        22

<210> SEQ ID NO 3
<211> LENGTH: 28
<212> TYPE: DNA
<213> ORGANISM: Artificial Sequence
<220> FEATURE:
<223> OTHER INFORMATION: PCR Forward Primer

<400> SEQUENCE: 3
cgggcacgta tgtgcgtttg ttgtttac                                  28

<210> SEQ ID NO 4
<211> LENGTH: 23
<212> TYPE: DNA
<213> ORGANISM: Artificial Sequence
<220> FEATURE:
<223> OTHER INFORMATION: PCR Reverse Primer

<400> SEQUENCE: 4
ttcctgggtt cggcggttga gtc                                       23